US009597185B2

(12) United States Patent
Braido et al.

(10) Patent No.: US 9,597,185 B2
(45) Date of Patent: Mar. 21, 2017

(54) LEAFLET-CUFF ATTACHMENTS FOR PROSTHETIC HEART VALVE

(71) Applicant: St. Jude Medical, Cardiology Division, Inc., St. Paul, MN (US)

(72) Inventors: Peter N. Braido, Wyoming, MN (US); Julia Ann Schraut, Shoreview, MN (US); Mina S. Fahim, Shoreview, MN (US); Andrea N. Para, Oakdale, MN (US); Kent J. Smith, Shoreview, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 101 days.

(21) Appl. No.: 14/568,253

(22) Filed: Dec. 12, 2014

(65) Prior Publication Data

US 2015/0173899 A1 Jun. 25, 2015

Related U.S. Application Data

(60) Provisional application No. 61/918,305, filed on Dec. 19, 2013.

(51) Int. Cl.
*A61F 2/24* (2006.01)

(52) U.S. Cl.
CPC .......... *A61F 2/2445* (2013.01); *A61F 2/2412* (2013.01); *A61F 2/2418* (2013.01); *A61F 2220/0075* (2013.01)

(58) Field of Classification Search
None
See application file for complete search history.

(56) References Cited

U.S. PATENT DOCUMENTS 3,657,744 A 4/1972 Ersek
4,275,469 A 6/1981 Gabbay
(Continued)

FOREIGN PATENT DOCUMENTS

DE 19857887 A1 7/2000
DE 10121210 A1 11/2002
(Continued)

OTHER PUBLICATIONS

"Holbein stitch", Wikipedia, https://en.wikipedia.org/wiki/Holbein_stitch, retrieved May 16, 2016.*
(Continued)

*Primary Examiner* — Thomas J Sweet
*Assistant Examiner* — Megan Wolf
(74) *Attorney, Agent, or Firm* — Lerner, David, Littenberg, Krumholz & Mentlik, LLP

(57) ABSTRACT

A prosthetic heart valve includes a stent having a collapsed condition and an expanded condition, the stent having a proximal end, a distal end and a plurality of commissure features. The heart valve further includes a valve assembly secured to the stent, the valve assembly including a cuff and a plurality of leaflets, each of the leaflets having a free edge having a first end and a second end, and a second edge secured to the cuff, the second edge having a first end, a second end, a first folded portion adjacent the first end, a second folded portion adjacent the second end, and an unfolded portion between the first and second folded portions. The first and second folded portions couple the leaflet to ones of the commissure features.

17 Claims, 16 Drawing Sheets

(56) References Cited

U.S. PATENT DOCUMENTS

| | | |
|---|---|---|
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,480,423 A | 1/1996 | Ravenscroft et al. |
| 5,843,167 A | 12/1998 | Dwyer et al. |
| 5,855,601 A | 1/1999 | Bessler et al. |
| 5,935,163 A | 8/1999 | Gabbay |
| 5,961,549 A | 10/1999 | Nguyen et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,685,625 B2 | 2/2004 | Gabbay |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo et al. |
| 7,311,730 B2 | 12/2007 | Gabbay |
| 7,374,573 B2 | 5/2008 | Gabbay |
| 7,381,218 B2 | 6/2008 | Schreck |
| 7,452,371 B2 | 11/2008 | Pavcnik et al. |
| 7,510,572 B2 | 3/2009 | Gabbay |
| 7,524,331 B2 | 4/2009 | Birdsall |
| RE40,816 E | 6/2009 | Taylor et al. |
| 7,585,321 B2 | 9/2009 | Cribier |
| 7,682,390 B2 | 3/2010 | Seguin |
| 7,731,742 B2 | 6/2010 | Schlick et al. |
| 7,803,185 B2 | 9/2010 | Gabbay |
| 7,846,203 B2 | 12/2010 | Cribier |
| 7,846,204 B2 | 12/2010 | Letac et al. |
| 7,914,569 B2 | 3/2011 | Nguyen et al. |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| D660,432 S | 5/2012 | Braido |
| D660,433 S | 5/2012 | Braido et al. |
| D660,967 S | 5/2012 | Braido et al. |
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0210304 A1 | 10/2004 | Seguin et al. |
| 2005/0096726 A1 | 5/2005 | Sequin et al. |
| 2005/0137695 A1 | 6/2005 | Salahieh et al. |
| 2005/0137697 A1 | 6/2005 | Salahieh et al. |
| 2005/0256566 A1 | 11/2005 | Gabbay |
| 2005/0273155 A1* | 12/2005 | Bahler ............... A61F 2/07 623/1.13 |
| 2006/0008497 A1 | 1/2006 | Gabbay |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0173532 A1 | 8/2006 | Flagle et al. |
| 2006/0178740 A1 | 8/2006 | Stacchino et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071361 A1 | 3/2008 | Tuval et al. |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0112309 A1 | 4/2009 | Jaramillo et al. |
| 2009/0138079 A1 | 5/2009 | Tuval et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0319991 A1 | 12/2011 | Hariton et al. |
| 2012/0123529 A1 | 5/2012 | Levi et al. |
| 2012/0197391 A1* | 8/2012 | Alkhatib ............ A61F 2/2418 623/2.18 |
| 2012/0316642 A1* | 12/2012 | Yu ............... A61F 2/2412 623/2.13 |
| 2015/0157455 A1* | 6/2015 | Hoang ............ A61F 2/2418 623/2.18 |

FOREIGN PATENT DOCUMENTS

| | | |
|---|---|---|
| DE | 202008009610 U1 | 12/2008 |
| EP | 0850607 A1 | 7/1998 |

(56) References Cited

FOREIGN PATENT DOCUMENTS

| | | |
|---|---|---|
| EP | 1000590 A1 | 5/2000 |
| EP | 1360942 A1 | 11/2003 |
| EP | 1584306 A1 | 10/2005 |
| EP | 1598031 A2 | 11/2005 |
| EP | 1926455 A2 | 6/2008 |
| EP | 2572676 A2 | 3/2013 |
| FR | 2847800 A1 | 6/2004 |
| FR | 2850008 A1 | 7/2004 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 03047468 A1 | 6/2003 |
| WO | 2006073626 A2 | 7/2006 |
| WO | 2007053243 A2 | 5/2007 |
| WO | 2007071436 A2 | 6/2007 |
| WO | 2008070797 A2 | 6/2008 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |
| WO | 2014004793 A2 | 1/2014 |

OTHER PUBLICATIONS

Catheter-implanted prosthetic heart valves, Knudsen, L.L., et al., The International Journal of Artificial Organs, vol. 16, No. 5 1993, pp. 253-262.

International Search Report and Written Opinion for Application No. PCT/US2014/069886 dated Mar. 6, 2015.

Is it Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.

Percutaneous aortic valve replacement: resection before implantation, 836-840, Quaden, Rene et al., European J. of Cardio-thoracic Surgery, 27 (2005).

Ruiz, Carlos, Overview of PRE-CE Mark Transcatheter Aortic Valve Technologies, Euro PCR, dated May 25, 2010.

Transluminal Aortic Valve Placement, Moazami, Nader, et al., ASAIO Journal, 1996; 42:M381-M385.

Transluminal Catheter Implanted Prosthetic Heart Valves, Andersen, Henning Rud, International Journal of Angiology 7:102-106 (1998).

Transluminal implantation of artificial heart valves, Andersen, H. R., et al., European Heart Journal (1992) 13, 704-708.

U.S. Appl. No. 29/375,243, filed Sep. 20, 2010.
U.S. Appl. No. 29/375,260, filed Sep. 20, 2010.

* cited by examiner

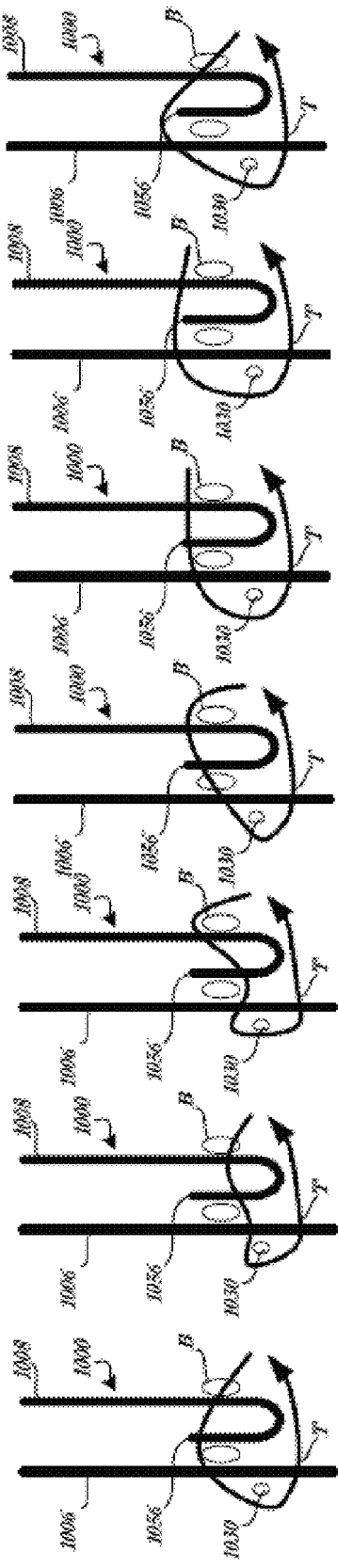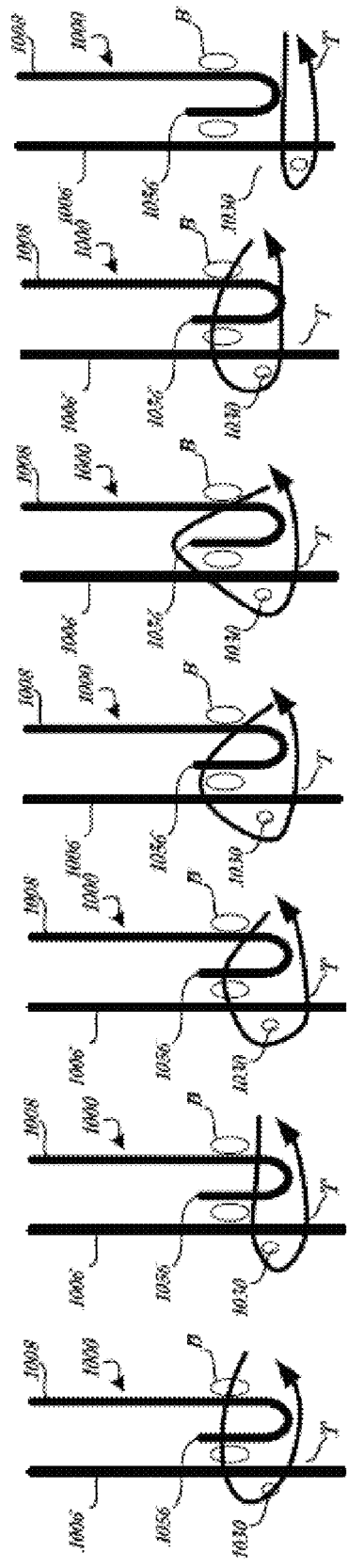

LEAFLET-CUFF ATTACHMENTS FOR PROSTHETIC HEART VALVE

CROSS-REFERENCE TO RELATED APPLICATIONS

The present application claims the benefit of the filing date of U.S. Provisional Patent Application No. 61/918,305 filed Dec. 19, 2013, the disclosure of which is hereby incorporated herein by reference.

BACKGROUND OF THE INVENTION

The present invention relates to heart valve replacement and, in particular, to collapsible prosthetic heart valves. More particularly, the present invention relates to collapsible prosthetic heart valves having unique valve leaflet attachments.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two common types of stents on which the valve structures are ordinarily mounted: a self-expanding stent and a balloon-expandable stent. To place such valves into a delivery apparatus and ultimately into a patient, the valve may first be collapsed or crimped to reduce its circumferential size and diameter.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating use range. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

BRIEF SUMMARY OF THE INVENTION

In some embodiments, a prosthetic heart valve includes a stent having a collapsed condition and an expanded condition, the stent having a proximal end, a distal end and a plurality of commissure features. The heart valve further includes a valve assembly secured to the stent, the valve assembly including a cuff and a plurality of leaflets, each of the leaflets having a free edge having a first end and a second end, and a second edge secured to the cuff, the second edge having a first end, a second end, a first folded portion adjacent the first end, a second folded portion adjacent the second end, and an unfolded portion between the first and second folded portions. The first and second folded portions couple the leaflet to ones of the commissure features.

In some embodiments, a prosthetic valve assembly includes a substantially cylindrical cuff, a plurality of leaflets disposed inside the cuff, a reverse-running stitch coupled to unfolded portions of each of the leaflets, the reverse-running stitch having an outer part disposed between the cuff and each of the leaflets and an inner part disposed on an opposite side of each of the leaflets and a suture for coupling the cuff to each of the leaflets.

BRIEF DESCRIPTION OF THE DRAWINGS

Various embodiments of the present invention are disclosed herein with reference to the drawings, wherein:

FIGS. 11C-P are highly schematic cross-sectional views of various configurations of attaching an underwire to a cuff;

Various embodiments of the present invention will now be described with reference to the appended drawings. It is to be appreciated that these drawings depict only some embodiments of the invention and are therefore not to be considered limiting of its scope.

DETAILED DESCRIPTION

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. When used in connection with devices for delivering a prosthetic heart valve into a patient, the terms "proximal" and "distal" are to be taken as relative to the user of the delivery devices. "Proximal" is to be understood as relatively close to the user, and "distal" is to be understood as relatively farther away from the user. Also, as used herein, the words "substantially," "generally" and "about" are intended to mean that slight variations from absolute are included within the scope of the structure or process recited.

Figure 1A:
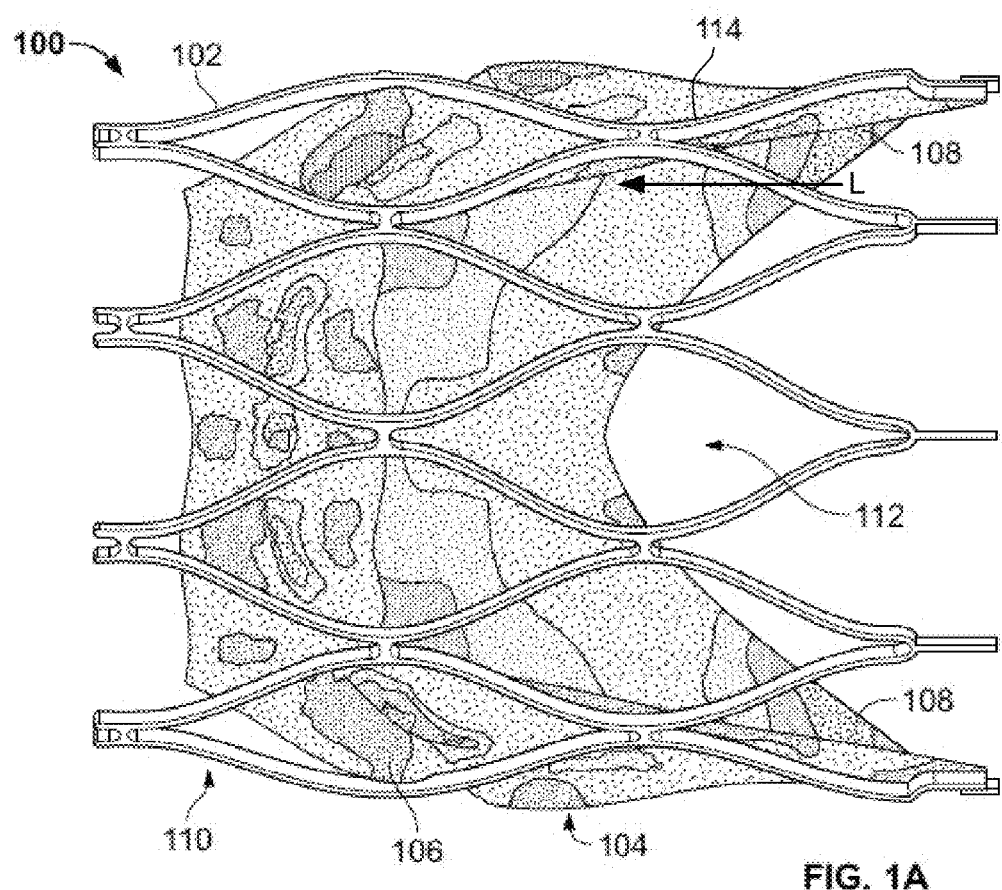
FIG. 1A is a partial side view of a prosthetic heart valve showing a potential strain distribution profile in the valve assembly.

FIG. 1A shows a typical collapsible prosthetic heart valve 100. The prosthetic heart valve 100 is designed to replace the function of a native aortic valve of a patient. Examples of collapsible prosthetic heart valves are described in International Patent Application Publication No. WO/2009/042196; U.S. Pat. Nos. 7,018,406; and 7,329,278, the disclosures of all of which are hereby incorporated herein by reference. As discussed in detail below, the prosthetic heart valve has an expanded condition and a collapsed condition. Although the invention is described herein as applied to a prosthetic heart valve for replacing a native aortic valve, the invention is not so limited, and may be applied to prosthetic valves for replacing other types of cardiac valves.

The prosthetic heart valve 100 includes a stent or frame 102, which may be wholly or partly formed of any biocompatible material, such as metals, synthetic polymers, or biopolymers capable of functioning as a stent. Suitable biopolymers include, but are not limited to, elastin, and mixtures or composites thereof. Suitable metals include, but are not limited to, cobalt, titanium, nickel, chromium, stainless steel, and alloys thereof, including nitinol. Suitable synthetic polymers for use as a stent include, but are not limited to, thermoplastics, such as polyolefins, polyesters, polyamides, polysulfones, acrylics, polyacrylonitriles, polyetheretherketone (PEEK), and polyamides. The stent 102 may have an annulus section 110, an aortic section (not shown), and an intermediate section (not shown) disposed between the annulus and aortic sections. Each of the annulus section 110, the intermediate section, and the aortic section of the stent 102 includes a plurality of cells 112 connected to one another around the stent. The annulus section 110, the intermediate section, and the aortic section of the stent 102 may include one or more annular rows of cells 112 connected to one another. For instance, the annulus section 110 may have two annular rows of cells 112. When the prosthetic heart valve 100 is in the expanded condition, each cell 112 may be substantially diamond shaped. Regardless of its shape, each cell 112 is formed by a plurality of struts 114. For example, a cell 112 may be formed by four struts 114.

The stent 102 may include commissure features or commissure posts (not shown) connecting at least two cells 112 in the longitudinal direction of the stent 102. The commissure features may include eyelets that facilitate the suturing of a valve assembly 104 to the stent 102.

The prosthetic heart valve 100 also includes a valve assembly 104 attached inside the annulus section 110 of the stent 102. United States Patent Application Publication No. 2008/0228264, filed Mar. 12, 2007, and United States Patent Application Publication No. 2008/0147179, filed Dec. 19, 2007, the entire disclosures of both of which are hereby incorporated herein by reference, describe suitable valve assemblies. The valve assembly 104 may be wholly or partly formed of any suitable biological material, fabric or a polymer. Examples of biological materials suitable for the valve assembly 104 include, but are not limited to, porcine or bovine pericardial tissue. Examples of polymers suitable for the valve assembly 104 include, but are not limited to, polyurethane and polyester.

The valve assembly 104 may include a cuff 106 disposed on the luminal surface of annulus section 110, on the abluminal surface of the annulus section, or on both surfaces, and the cuff may cover all or part of either or both of the luminal and abluminal surfaces of the annulus section. FIG. 1A shows cuff 106 disposed on the luminal surface of annulus section 110 so as to cover part of the annulus section while leaving another part thereof uncovered. In addition to the materials for forming valve assembly 104 noted above, the cuff 106 and/or any of the sutures described herein may include ultra-high-molecular-weight polyethylene. The valve assembly 104 may further include a plurality of leaflets 108 which collectively function as a one-way valve.

Figure 1B:
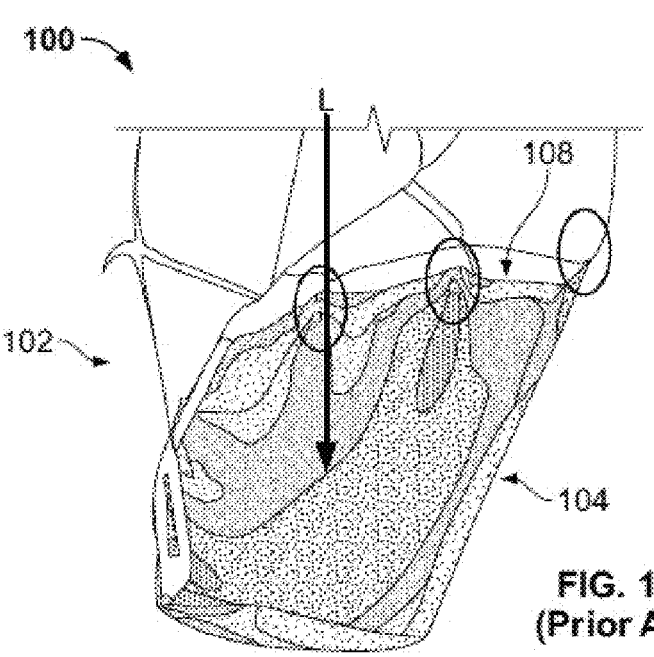
FIG. 1B is an enlarged partial view of the prosthetic heart valve of FIG. 1A showing the strain distribution in the leaflet.

The cuff 106 of the prosthetic heart valve 100 of FIG. 1A tends to experience relatively high strain and/or stress at certain locations. In such heart valves 100, the pressure of blood that leaflets 108 keep from flowing into the heart may subject leaflets 108 to a load in the direction indicated by arrow L, shown in FIG. 1B. This load may cause high stress and/or strain on the cuff and/or leaflets. Moreover, a typical load may cause wear over time. To manage the increased stress and strain on the cuff 106, some conventional heart valves 100 have made the cuff thicker. However, thicker cuffs generally lead to a larger heart valve that is more difficult to deliver and implant.

One method of redistributing the load has been to attach the leaflets to the struts. Alternatively, it may be advantageous to attach the leaflets substantially entirely to the cuff and not to the struts. In certain procedures, collapsible valves may be implanted in a native valve annulus without first resecting the native valve leaflets. Additionally, other patients may have uneven calcification, bi-cuspid disease, and/or valve insufficiency.

To reduce adverse events, (e.g., (1) perivalvular leakage (PV leak), (2) valve migration, (3) mitral valve impingement, (4) conduction system disruption, (5) coronary blockage, etc.) adequate sealing and anchoring without excessive radial force may be advantageous. Embodiments of the present invention which attach the leaflets mainly to the cuff are able to achieve better coaptation of the leaflets, reducing the risk of leakage.

Moreover, the annulus section of the prosthetic valve may have a generally regular cylindrical shape by which is meant that the structure has a generally circular cross-section with a substantially constant diameter along its length. When placed in the annulus of a native heart valve, such as, for example, the tricuspid aortic valve, and expanded, a substantially fluid-tight fit should result. However, the native valve annulus may not be circular, and, in fact, may vary from patient to patient, as may the shape of the aortic sinus or aorta, the angle of the junction between the valve annulus and the aortic sinus, and other local anatomical features. When a prosthetic valve is deployed and expanded, it is advantageous that it accommodates these anatomical variations in order to function properly. This may result in distortion of the shape of the stent and/or valve assembly, and the repositioning of leaflets relative to one another, which can affect the coaptation of these leaflets.

As the stent of a collapsible prosthetic heart valve distorts during implantation, during beating of the heart, or because of irregularities in the patient's anatomy or the condition of the native valve, such distortion may be translated to the valve assembly, such that not all of the valve leaflets meet to form effective coaptation junctions. This can result in leakage or regurgitation and other inefficiencies which can reduce cardiac performance. Moreover, if the prosthetic valve is not placed optimally and the valve leaflets are not coapting as intended, other long term effects, such as uneven wear of the individual leaflets or increased stress on the cuff and/or stent, may be postulated.

Prosthetic valves in accordance with certain aspects of the present invention, however, can function properly notwithstanding the distortion of the stent and/or valve assembly because the leaflets are substantially attached to the cuff and not to the stent. Without wishing to be held to any particular theory, it is believed that a valve design having leaflets mostly sewn to the cuff may be better able to adjust to less than perfect annulus geometry. Such leaflet-cuff arrangements may be more insulated from imperfect geometry-induced stresses on the struts than those arrangements having the leaflets completely or predominantly sewn to the stent. Thus, the possibility of uneven wear due to anatomical variations is greatly reduced by attaching the leaflets entirely or predominantly to the cuff.

Moreover, by sewing the leaflets to the cuff and not to the struts, greater flexibility is afforded in positioning the leaflets and in varying the height, width and shape of the leaflets. Specifically, because the leaflets in conventional heart valves are attached to the struts, the leaflet shape and positioning is limited by the location of the struts. In contrast, suturing patterns may be varied with greater benefits when the leaflets are attached predominantly to the cuff.

Having outlined some of the benefits of a leaflet-cuff attachment, the features of this embodiment will be described in connection with the prosthetic heart valve 300 shown in FIGS. 2A-5. It will also be noted that while the inventions herein described are predominately discussed in terms of a tricuspid valve and a stent having a shape as illustrated in FIGS. 2A-5, the valve could be a bicuspid valve, such as the mitral valve, or include more than three leaflets, and the stent could have different shapes, such as a flared or conical annulus section, a less-bulbous aortic section, and the like, and a differently shaped intermediate section.

In attaching the plurality of leaflets, each leaflet 308 may be first attached to the stent 302 by suturing through the eyelets of commissure features 316. Additional examples of leaflet-commissure feature attachments are disclosed in U.S. patent application Ser. No. 13/216,124, entitled "Leaflet Suturing to Commissure Points for Prosthetic Heart Valve", filed on Aug. 23, 2011, the disclosure of which is hereby incorporated by reference as if fully set forth herein. In addition to the commissure features 316, the plurality of leaflets may be attached to the cuff 306 as described below.

Figure 2A:
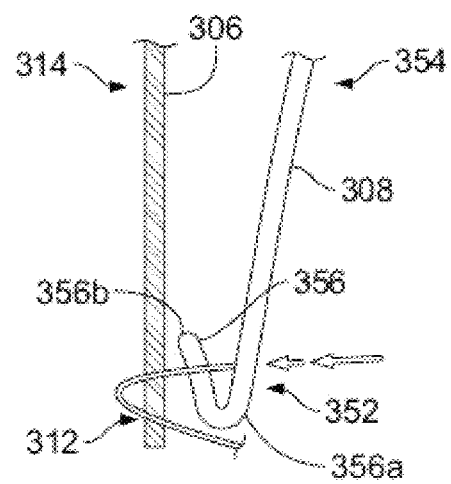
FIG. 2A is a highly schematic cross-sectional view of a portion of a collapsible prosthetic heart valve according to the present invention having folded leaflets sutured to the cuff.
Figure 2B:
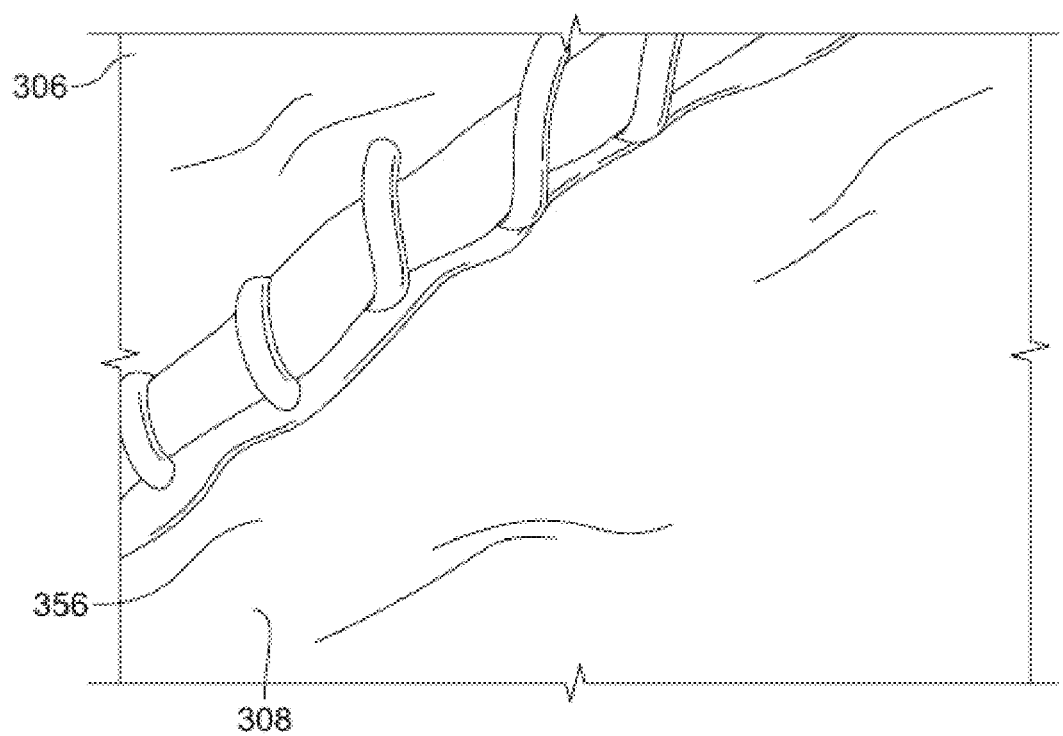
FIG. 2B is an enlarged side view of a portion of a collapsible prosthetic heart valve according to the present invention showing a folded belly flap.
Figure 3:
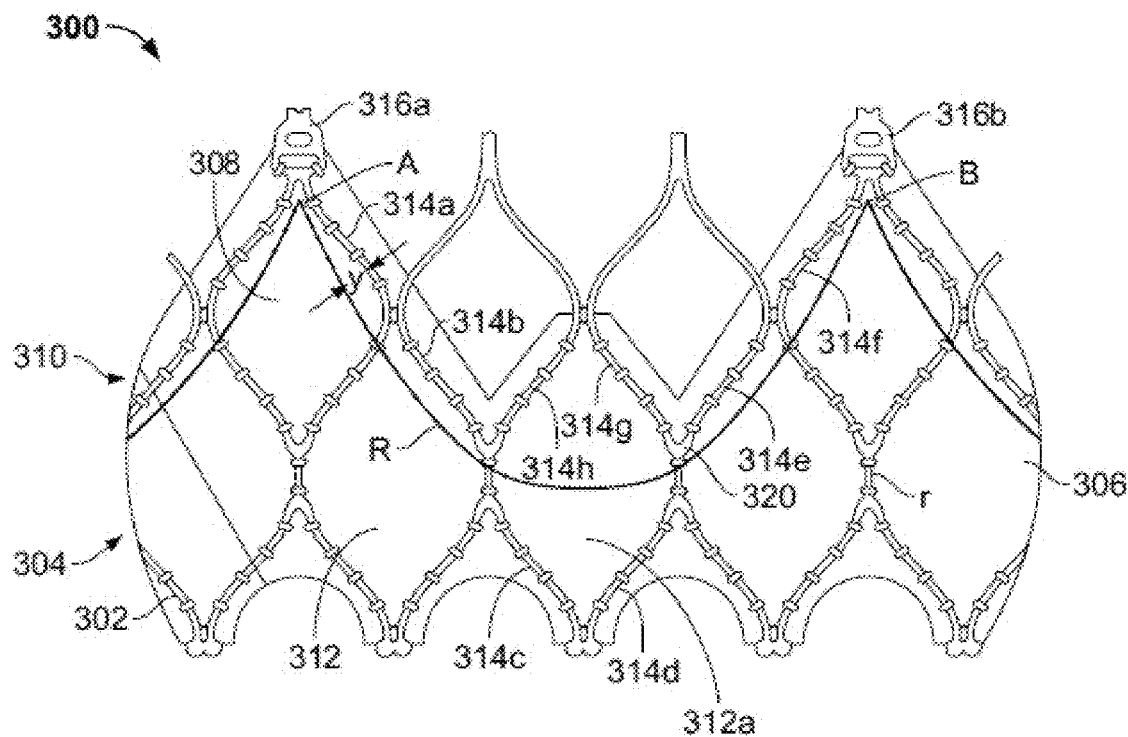
FIG. 3 is a partial developed view of a collapsible prosthetic heart valve according to the present invention showing the suturing pattern of the leaflets to the cuff.

FIGS. 2A, 2B and 3 illustrate one such embodiment in which the leaflets 308 have been attached by suturing substantially entirely to the cuff 306. In the illustrated embodiment, the leaflets 308 are coupled to the cuff 306 after they have been attached to the commissure features 316. It will be understood, however, that the order of attachment may be changed or varied as necessary by those skilled in the art.

FIGS. 2A and 2B illustrate a cuff 306 and one or more leaflets 308. Each leaflet 308 includes a proximal end 352 for attachment to the cuff 306 and a free distal end 354 for coapting with the other leaflets to form a closed valve. As seen in FIG. 2A, each leaflet 308 may be folded upon itself at the proximal end 352 to form a belly flap 356 for attaching the leaflet to the cuff 306. The belly flap 356 may be formed by folding the proximal end of the leaflet 308 once over itself toward the cuff 306 so that the belly flap is disposed between a portion of the leaflet and the cuff. The width x of the belly flap 356 between fold line 356a and free edge 356b may vary from valve to valve, and also within a valve. For example, the belly flap 356 may have a width x between about 0.1 mm and about 2.0 mm. Variants of the belly flap 356 are also contemplated herein. For example, the belly flap 356 may be formed by folding the leaflet 308 more than once (e.g., twice, thrice or more). Additionally, the belly flap 356 may be formed along only a portion of the proximal end of the leaflet 308 if the entire proximal end will not be sutured to the cuff 306. Still further, the belly flap 356 may be formed by folding the proximal end of the leaflet 308 away from the cuff 306, rather than toward the cuff as described above.

After folding each leaflet 308 to form a belly flap 356, the leaflets 308 may be attached to the cuff 306 in accordance with the attachment pattern shown in FIG. 3. For the purpose of clarity, the leaflet-cuff attachment pattern will be described with reference to FIG. 3 without showing a belly flap. It will be understood, however, that a belly flap as described above and shown in FIGS. 2A and 2B may be disposed either on the inner or luminal side of the leaflet 308 or between the leaflet and the cuff 306.

The prosthetic heart valve 300 of FIG. 3 includes a stent or frame 302 having an annulus section 310 and an aortic section (not shown). Each of the annulus section 310 and the aortic section of the stent 302 includes a plurality of cells 312 connected to one another around the circumference of the stent. The annulus section 310 and the aortic section of the stent 302 may include one or more annular rows of cells 312 connected to one another. For instance, the annulus section 310 may have two annular rows of cells 312. When the prosthetic heart valve 300 is in the expanded condition, each cell 312 may be substantially diamond shaped. Regardless of its shape, each cell 312 is formed by a plurality of struts 314. For example, a cell 312 may be formed by four struts 314.

The stent 302 may include commissure features 316 connecting at least two cells 312 in the longitudinal direction of the stent. The commissure features 316 may include eyelets for facilitating the suturing of a valve assembly 304 to the stent 302.

A cuff 306 may be disposed on the luminal surface of annulus section 310, on the abluminal surface of the annulus section, or on both surfaces, and the cuff may cover all or part of either or both of the luminal and abluminal surfaces of the annulus section. FIG. 3 shows cuff 306 disposed on the luminal surface of annulus section 310 so as to cover part of the annulus section while leaving another part thereof uncovered. In particular, the cuff 306 covers substantially all of the annulus section 310 between the proximal edge of stent 302 and the commissure features 316, but a much lesser area of the annulus section between the commissure features. The valve assembly 304 may further include a plurality of leaflets 308 which collectively function as a one-way valve.

As shown in FIG. 3, struts 314a, 314b, and 314c may be connected to one another in substantially end-to-end fashion diagonally along three cells 312, beginning with an end of the strut 314a connected to a commissure feature 316a and ending with an end of strut 314c connected to an end of strut 314d. Struts 314c and 314d are part of the same cell 312a. Struts 314d, 314e, and 314f may be connected to one another in substantially end-to-end fashion diagonally along three cells 312, beginning with an end of the strut 314f connected to a commissure feature 316b and ending with the connection between an end of strut 314d and an end of strut 314c. For the sake of completeness, cell 312a includes strut 314c connected to strut 314d at the bottom of the cell and struts 314g and 314h connected to one another at the top of the cell, as well as to struts 314d and 314c, respectively.

In addition to being connected to one another around the circumference of stent 302, cells 312 may be connected to one another in the longitudinal direction of the stent. Two adjacent struts, for example struts 314e and 314g, merge near the bottom of the cell before splitting off into two different struts. The meeting point where two struts 314 merge or where one strut splits into two components is defined as an ancon 320. The ancons 320 in two longitudinally adjacent rows of cells 312 may be joined by runners r.

The plurality of leaflets 308 may be attached directly to the cuff 306 near struts 314a, 314b, 314e, and 314f, such as by suturing. As shown in FIG. 3, the leaflets 308 may be attached to cuff 306 just proximally of the aforementioned struts 314 along an attachment line R. Specifically, a distance y may be maintained between the attachment line R and the struts 314. This distance may be greater than, less than or equal to 2.0 mm, and may vary as necessary. By attaching the leaflets 308 to the cuff 306 in a pattern that follows the curvature of some of the struts 314, stress on the cuff 306 may be reduced while maintaining a degree of flexibility.

As described above, the attachment line R includes an initial descent from just proximal of commissure feature 316a and continues proximally of struts 314a and 314b while substantially maintaining a distance y from the struts. At the proximal end of strut 314b, the attachment line R begins to flatten out, passing through cell 312a, and then ascends proximally of struts 314e and 314f, maintaining substantially the same or a similar distance y from the struts, until it reaches a point just proximal of commissure feature 316b. Between the descending seam and the ascending seam, the attachment line may cross a pair of runners r1 and r2 and form a vertex therebetween. In at least some other examples, attachment line R may pass above or below at least one of the runners r1 and r2.

Figure 4:
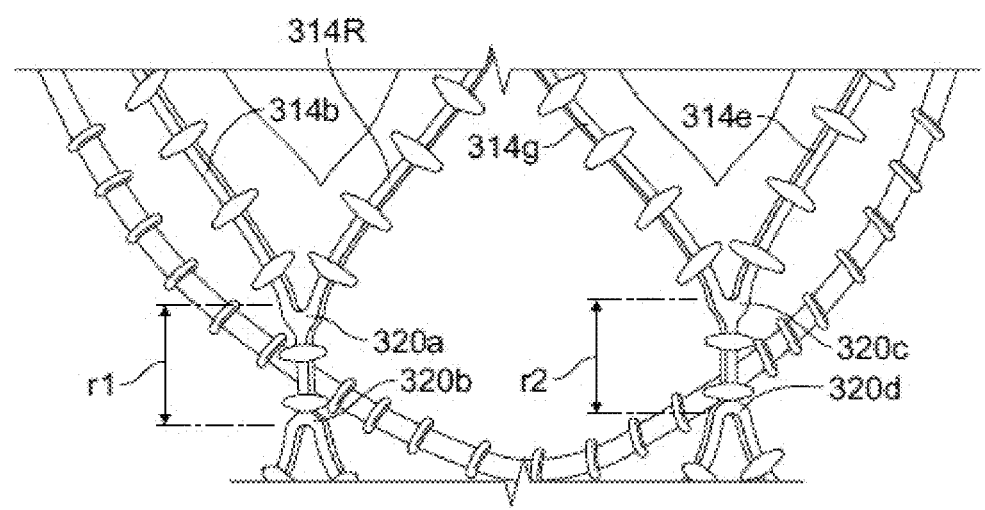
FIG. 4 is an enlarged side view of a portion of the collapsible prosthetic heart valve of FIG. 3 showing the runner region between ancons.

FIG. 4 shows runners r1 and r2 in more detail. As described above, the attachment line R generally descends from a point just proximal of commissure feature 316, travels proximally of struts 314a and 314b, crosses runner r1, changes direction and crosses runner r2, and then ascends proximally of struts 314e and 314f until it reaches a point just proximal of commissure feature 316b.

The foregoing discussion describes the general pattern by which leaflets 308 may be attached directly to cuff 306. Having generally described the attachment pattern, the following description provides one exemplary method of suturing the leaflets 308 to the cuff 306. As will be understood by those of ordinary skill in the art, the description below is for one of many possible methods, and the distances, configurations and arrangements described are merely exemplary and not limiting. For example, instead of using a single suture around the perimeter of the valve assembly, leaflets 308 may be sutured to the cuff 306 using a plurality of sutures, staples, bioglue or any other suitable method of attachment.

Initially, the leaflets 308 are aligned with the cuff 306 and struts 314 at the desired locations, typically in the annulus section 310. The ends of the distal free edge of each leaflet 308 are then sutured to both the cuff 306 and the stent 302 through the eyelets of an adjacent pair of commissure features 316. The belly of the leaflets 308 may then be sutured to the cuff 306 around the circumference of the heart valve 300 proximally of the commissure features 316.

With reference to FIG. 3, a first leaflet 308 may be sutured to the cuff 306 by first passing a suture from the abluminal side of the cuff 306 to the luminal side of the cuff about 0.5 mm to about 2.0 mm proximally of a first commissure feature 316a. This location will be referred to as the origination stitch. A suture tail segment may be maintained at the origination stitch in order to tie to the end of the pattern after stitching around the circumference of the cuff 306 has been completed. The leaflet 308 may then be stitched to the cuff 306 using a series of whip stitches. In at least some other examples, a running, or reverse-running stitch may be used instead of a whip stitch. Stitches from the abluminal side to the luminal side of the heart valve 300 pass through the cuff 306 only. Stitches from the luminal side to the abluminal side of the heart valve 300 pass through both layers of the leaflet 308 (e.g., the leaflet as well as the folded belly flap 356) and the cuff 306. Thus, with each whip stitch the suture is passed from the abluminal side to the luminal side of the heart valve 300 through the cuff 306 only and then through both layers of the leaflet 308 and the cuff 306 from the luminal side of the valve to the abluminal side thereof.

The stitch spacing and bite size may vary. In at least some examples, the stitch spacing and bite size may be from about 0.5 mm to about 2.0 mm, and preferably is about 1.0 mm. Stitches may be approximately perpendicular to the leaflet edge when viewed from the side of the valve 300. Beginning just proximally of commissure feature 316a, the sutures may travel approximately at a distance y proximally of struts 314a and 314b, across a first runner r1, form a vertex, across a second runner r2, and approximately at a distance y proximally of struts 314e and 314f until reaching a point just proximal of commissure feature 316b. The sutures may begin at a point A about 0.5 mm to about 2.0 mm proximal of commissure feature 316a, and may end at a point B about 0.5 mm to about 2.0 mm proximal of commissure feature 316b.

Thus, between the first commissure feature 316a and the second commissure feature 316b, a substantially symmetrical parabola is formed by the suture line R. This parabolic pattern may be repeated between commissure features 316b and 316c and between commissure features 316c and 316a around the circumference of the cuff 306, ending at or near point A where the suture line R began. Upon returning to point A, the concluding tail of the suture line R may be tied to the origination stitch using a single double knot or any other suitable knot.

Figures 5A, 5B:
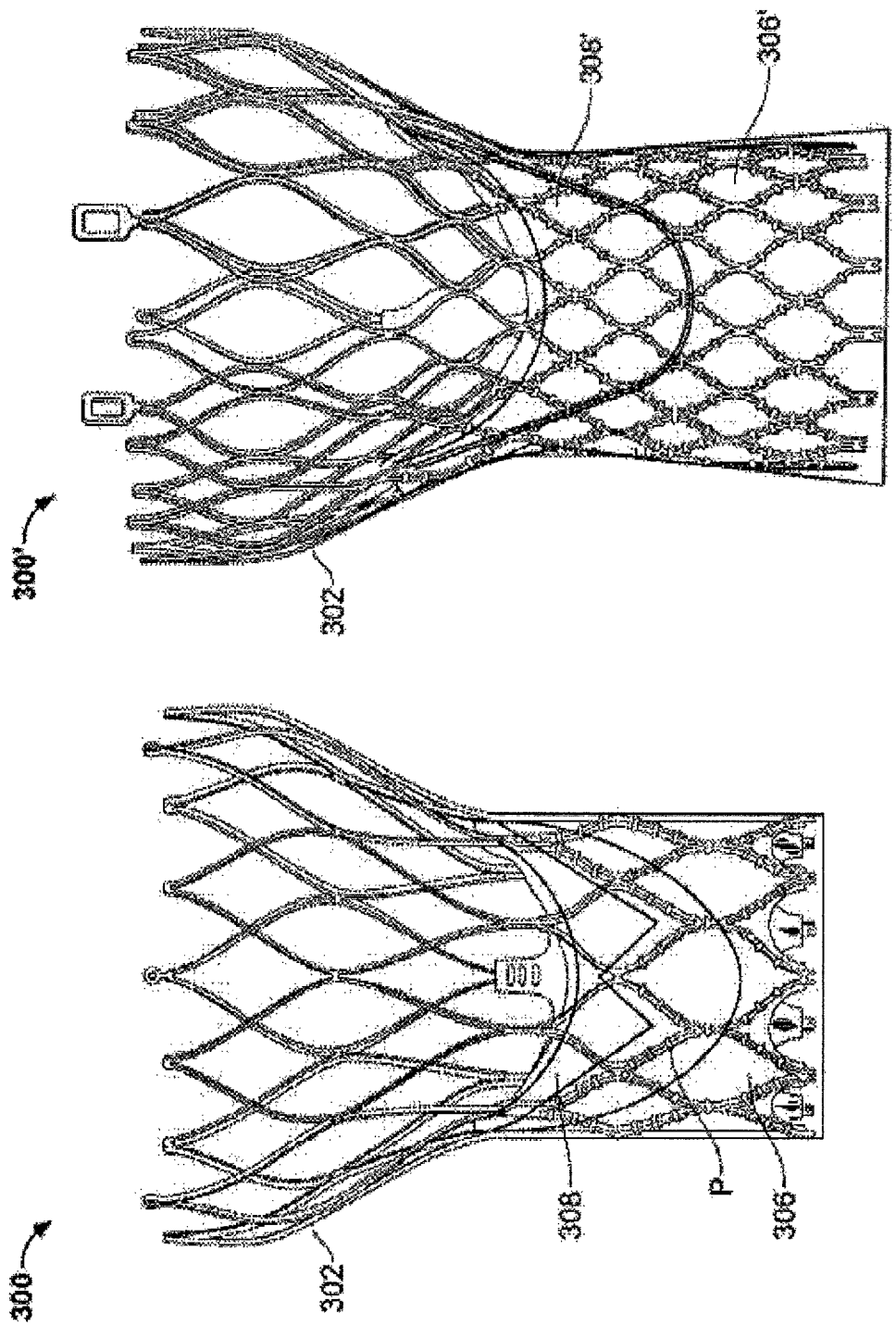
FIGS. 5A and 5B are side views of a collapsible prosthetic heart valve according to the present invention having a tissue pocket between the cuff and the leaflet, and a prior art device lacking such a pocket, respectively.

FIGS. 5A and 5B show a comparison between a heart valve 300 according to one embodiment of the present invention and a conventional heart valve 300'. As can be seen, the heart valve 300 according to the present invention includes an enlarged cuff 306 that overlaps with a portion of the leaflets 308. In contrast, the heart valve 300' includes no such overlap between the leaflets 308' and the cuff 306'. Rather, the leaflets 308' and cuff 306' are attached to one another in an edge-to-edge fashion. The leaflet-cuff overlap provided by the heart valve 300 of the present invention forms a pocket P and allows for the suture pattern discussed above. Pocket P formed by the leaflet-cuff overlap minimizes perivalvular leakage and acts as a tissue buffer for improved durability. Compared to conventional devices, this configuration also provides a larger buffer against fretting corrosion. Thus, by providing an enlarged cuff, the stress on the cuff may be decreased, the durability of the cuff increased and the flexibility of the heart valve increased to allow for applications such as partial deployment of the heart valve, for example, for testing.

In this manner, by attaching the leaflets 308 to the cuff 306, a host of benefits as enumerated above, as well as others, may be achieved. Moreover, the description above provides one method by which stress on the cuff can be reduced. Namely, by suturing the leaflets to the cuff, maintaining the spacing between the suture line and the struts described above, and passing the sutures across the runners, the load on the cuff can be partially redistributed to the struts to prevent possible wear and/or failure. Thus, the foregoing embodiment describes one method for reducing stress on the cuff at critical junctions. This method provides a solution by suturing the leaflets to the cuff without providing a thicker cuff or using different materials for the cuff.

The above embodiment notwithstanding, it will be understood that the leaflets need not be coupled only (except for the commissure features) to the cuff. In other embodiments, instead of suturing the leaflets to only the cuff, selected regions of each leaflet, or the proximal edge thereof, may be attached to an underwire disposed on or coupled to the cuff to relieve additional stress from the cuff. These embodiments will be described in more detail with reference to FIGS. 6-11.

Figure 6:
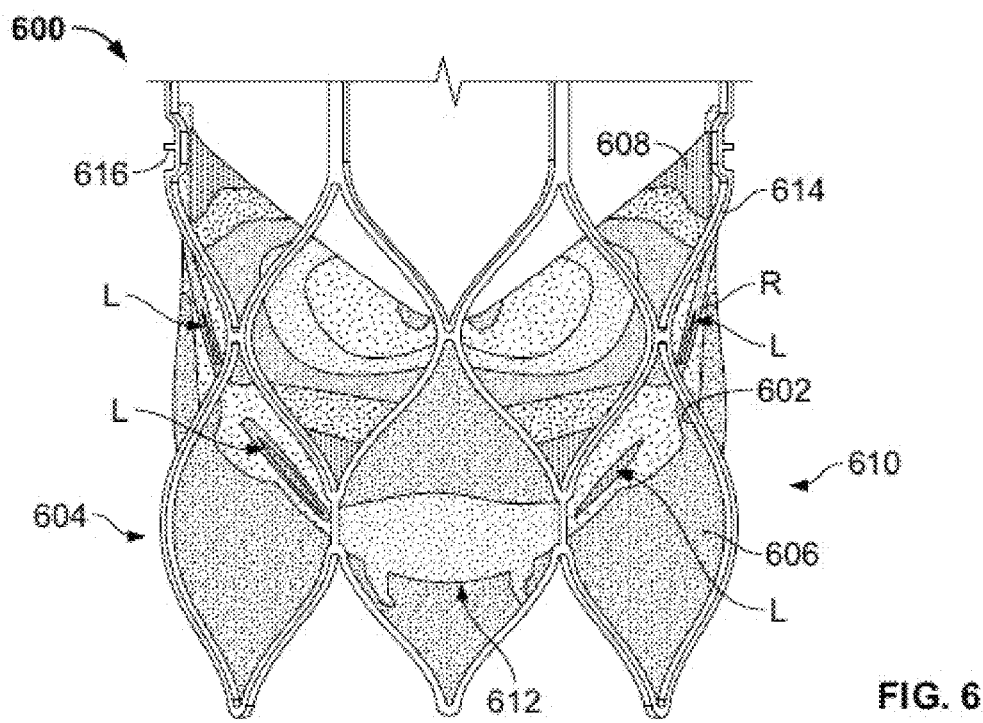
FIG. 6 is a partial side view of a prosthetic heart valve showing the leaflet-cuff attachment load distribution in the valve assembly.

FIG. 6 is a partial side view of a prosthetic heart valve 600 having a stent 602 and a valve assembly 604 disposed in the annulus section 610 of the stent. Within the heart valve 600, leaflets 608 are attached to cuff 606 via sutures. FIG. 6 shows a potential leaflet-cuff attachment load distribution in the valve assembly. When leaflets 608 coapt to form a closed configuration, load is transferred from the leaflet structure to the attachment points along the leaflet belly contour. As described in the above embodiments, these attachment points coincide with attachment line R. The load distribution diagram shows that high point loads are generated at individual sutures at certain regions L along attachment line R. If the point loads at regions L are sufficiently high, they will pull the suture through the material of the cuff 606. Repetitive wear may pull the suture through the material of cuff 606. Thus, regions L may be prone to failure. This failure may occur by tearing of the cuff 606, the leaflet 608, the sutures attaching the cuff 606 to the leaflet 608 or any combination thereof.

According to the present invention, a suture underwire may be attached to the prosthetic heart valve externally of the cuff to redistribute the load at the points at which the leaflets attach to the cuff, reducing the risk of valve structural damage due to a break in the joint/subassembly formed between the cuff and the leaflet attachment line R. Without being bound to any particular theory, it is believed that the underwire may improve cuff durability, improve valve function, reduce perivalvular leakage due to cuff billowing, achieve an optimal leaflet contour and aid in reducing the implant catheter profile.

Figure 7A:
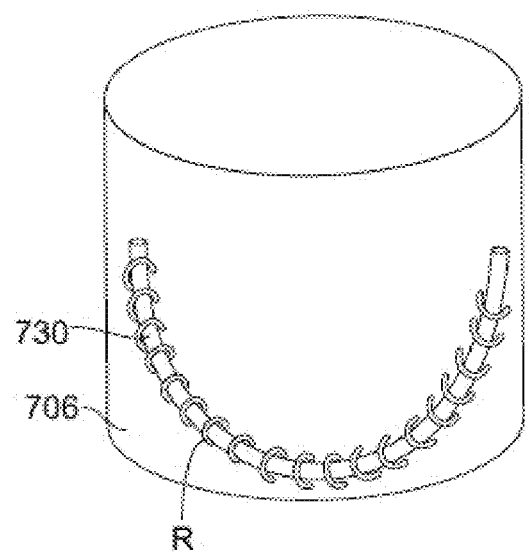
FIG. 7A is a highly schematic perspective view of an underwire secured to a cuff.
Figure 7B:
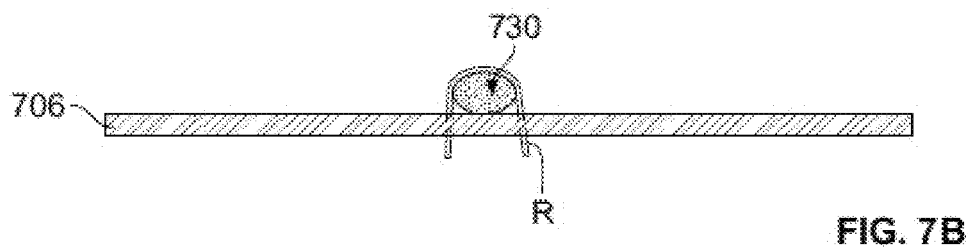
FIG. 7B is a highly schematic top view of an underwire secured to a cuff.

FIG. 7A is a highly schematic view of an underwire 730 secured to a cuff 706 according to an embodiment of the present invention. The underwire 730 may be formed of a suture, wire, fabric, polymers, reinforced polymers, a metal such as nitinol, a biomaterial such as pericardial tissue, stainless steel or the like, or any combination thereof, such as a braided wire or metal-suture combination. In some examples, underwire 730 may be formed of an ultra-high-molecular-weight polyethylene, such as FORCE FIBER®. The underwire 730 may also be formed as a solid rod, a tube or a wire to provide support at certain portions of the cuff 706. In one specific embodiment, the underwire 730 may be formed of a nitinol wire that is heat-set to the counter of the cuff 706. As seen in the schematic view of FIG. 7A, the underwire 730 may be attached to the cuff in a parabolic pattern complementing attachment line R. The attachment patterns and configurations of underwire 730 will be discussed in more detail below. It is sufficient from this diagram and from the highly schematic diagram of FIG. 7B to appreciate that the underwire 730 will assist in supporting the suturing between the cuff 706 and the leaflets 708 by providing a reinforcement to redistribute the load between the leaflets and the cuff.

Figure 8:
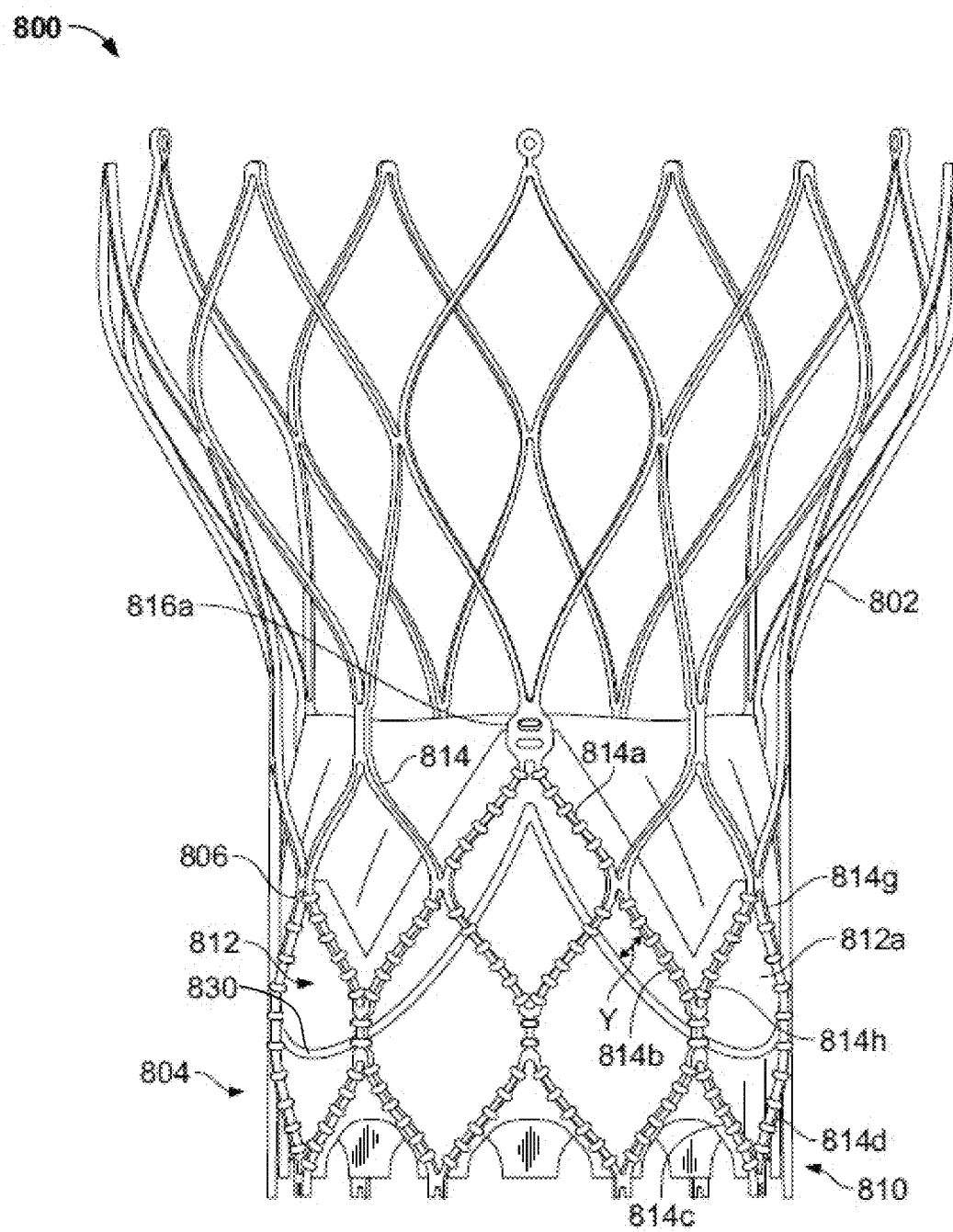
FIG. 8 is a side view of a collapsible prosthetic heart valve having an underwire.
Figure 9A:
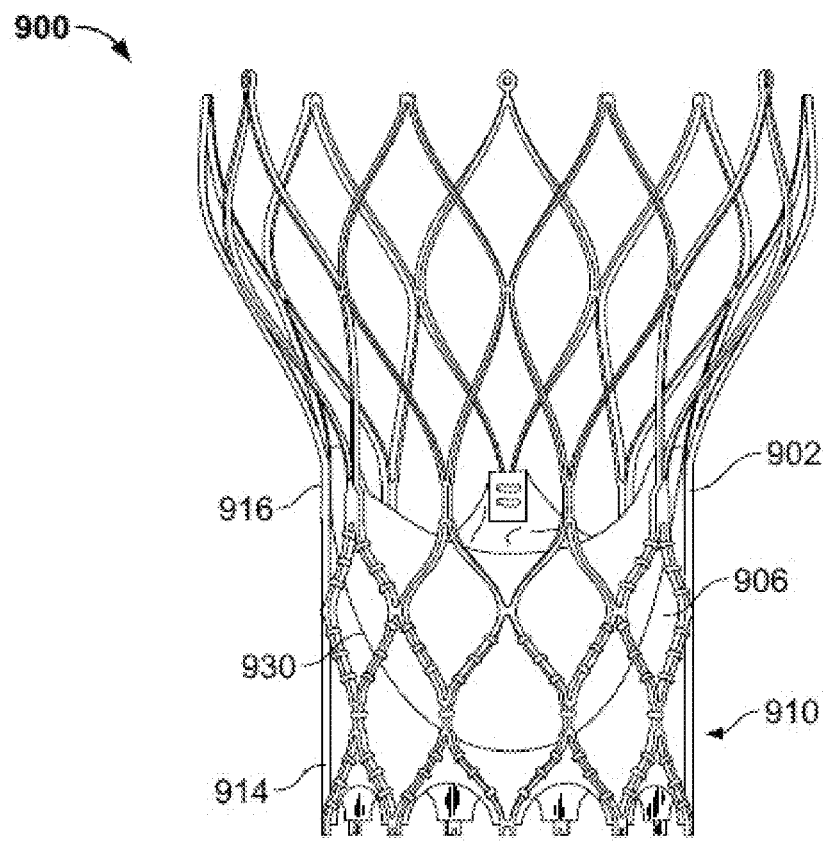
FIG. 9A is a side view of another collapsible prosthetic heart valve having an underwire.
Figure 9B:
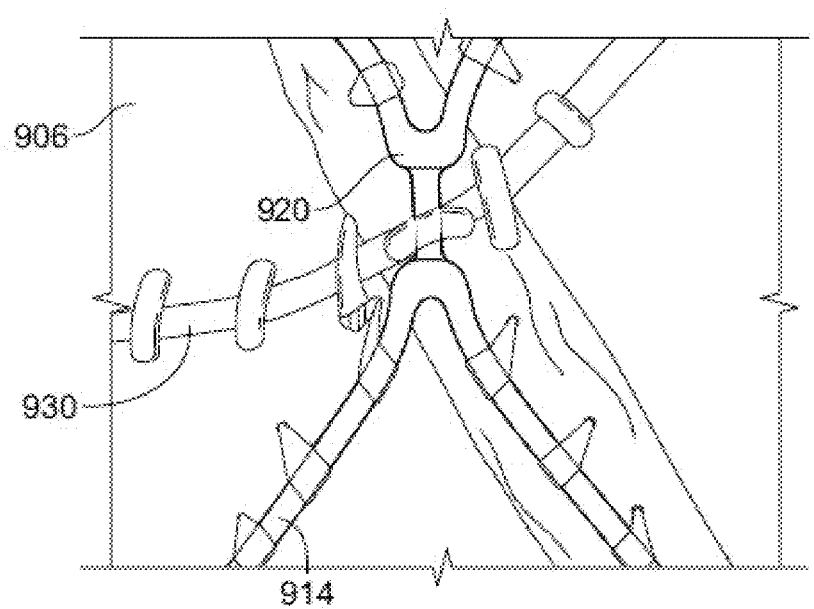
FIG. 9B is an enlarged side view of a portion of the collapsible prosthetic heart valve of FIG. 9A showing the underwire crossing struts.

FIGS. 8, 9A and 9B describe several patterns for attaching the underwire to the cuff. Though these specific attachment patterns are described herein, it will be understood that any of the patterns described above with reference to attachment line R of FIG. 3 may be used for attaching the underwire to the cuff. The attachment line may be sutured around or through the underwire to provide additional support. Moreover, it will be understood that the underwire may be attached to the cuff prior to suturing the leaflets to the cuff. For example, the underwire may be attached to the cuff before attaching the cuff to the stent or after attaching the cuff to the stent. Additionally, the underwire may be attached to the cuff at the same time that the leaflets are sutured to the cuff.

In a first example, shown in FIG. 8, a prosthetic heart valve 800 includes a stent 802 and a valve assembly 804 disposed in the annulus section 810 of the stent. A cuff 806 is attached to the stent 802 on the luminal side of annulus section 810. Stent 802 includes a plurality of struts 814 connected to one another to define open cells 812. Struts 814a, 814b, and 814c may be connected to one another in substantially end-to-end fashion diagonally along three cells 812, beginning with an end of the strut 814a connected to a commissure feature 816a and ending with an end of strut 814c connected to an end of strut 814d. Struts 814c and 814d are part of the same cell 812a. For the sake of completeness, cell 812a includes strut 814c connected to strut 814d at the bottom of the cell and struts 814g and 814h connected to one another at the top of the cell, as well as to struts 814d and 814c, respectively.

Underwire 830 may form a pattern around the circumference of cuff 806. As with the attachment line R described above, the pattern of underwire 830 may likewise include an initial descent from just proximal of commissure feature 816a and may continue proximally of struts 814a and 814b while substantially maintaining a distance y from the struts. At the proximal end of strut 814b, the pattern of underwire 830 begins to flatten out, passing through cell 812a, and then ascends proximally of the next set of struts (not shown in FIG. 8), until it reaches a point just proximal of the next commissure feature. It should be noted that the underwire 830 in FIG. 8 is attached to the cuff 806 and is disposed between the cuff and the stent 802. With this arrangement, loads from the underwire 830 are distributed directly to the cuff 806 only and not to the struts 814. Additionally, the pattern of underwire 830 in the embodiment of FIG. 8 begins and ends at points proximal of the commissure features 816 as discussed.

FIG. 9A is a side view of a second example of the attachment of an underwire 930 to a cuff 906. The prosthetic heart valve 900 is similar to the prosthetic heart valve 800 described above, and therefore like elements are identified by like reference numerals that begin with the numeral "9", instead of the numeral "8". The manner of attachment for underwire 930 is similar to the manner of attachment for underwire 830, with two exceptions. First, underwire 930 is attached directly to commissure features 916 instead of ending at points proximal of the commissure features. In addition, the underwire 930 is disposed outwardly of stent 902 as shown in the enlarged view of FIG. 9B. That is, stent 902 is disposed between cuff 906 and underwire 930. By attaching underwire 930 to the commissure features 916 and/or by passing underwire 930 outwardly of stent 902, loads may be redistributed from the underwire to the stent struts 914.

It should be understood that any combination of these arrangements may be utilized to attach the underwire 930 to the cuff 906. For example, underwire 930 may be arranged between cuff 906 and stent 902 as described in FIG. 8, but also may attach to the commissure features 916 as described in FIG. 9. Alternatively, underwire 930 may be arranged outwardly of stent 902 at select points only or may be attached to select commissure features or no commissure features. In this manner, the load may be distributed from the underwire to the cuff and/or the stent as desired.

Having described the manner of attaching the underwire to the cuff and stent, some possible arrangements for attaching the leaflets to the cuff and underwire will now be described. Several alternatives for such attachment are shown in FIGS. 10A-C.

Figure 10A:
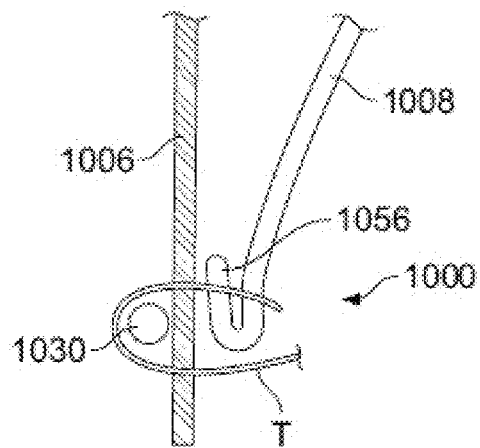
FIG. 10A is a highly schematic cross-sectional view of a portion of a collapsible prosthetic heart valve according to the present invention having a folded leaflet sutured to the underwire and the cuff.

FIG. 10A is a highly schematic cross-sectional view of a portion of a collapsible prosthetic heart valve 1000 according to one example of the present invention. Heart valve 1000 has leaflets 1008 sutured to both an underwire 1030 and a cuff 1006. Each leaflet 1008 may be folded upon itself at its proximal end to form a belly flap 1056 for attaching the leaflet 1008 to the cuff 1006. The belly flap 1056 may take any of the configurations or arrangements discussed above with reference to FIG. 2A or may not include a fold at all. The structure of heart valve 1000 as described in connection with FIG. 10A may be the same for FIGS. 10B and 10C.

The manner in which leaflets 1008 are attached to cuff 1006 and underwire 1030, as in FIG. 10A, will be referred to as the "wrapped" configuration. In this wrapped configuration, leaflet 1008 is folded upon itself to form belly flap 1056. A suture T begins from the interior of valve 1000 and passes through the leaflet 1008, the leaflet belly flap 1056, and the cuff 1006. The suture T then wraps around underwire 1030 and is passed back toward the interior of the valve through the cuff 1006 and under the folded edge of leaflet 1008, creating a whip stitch. This stitch pattern may be repeated around the entire circumference of valve 1000 to secure each of leaflets 1008 and underwire 1030 to cuff 1006.

Figure 10B:
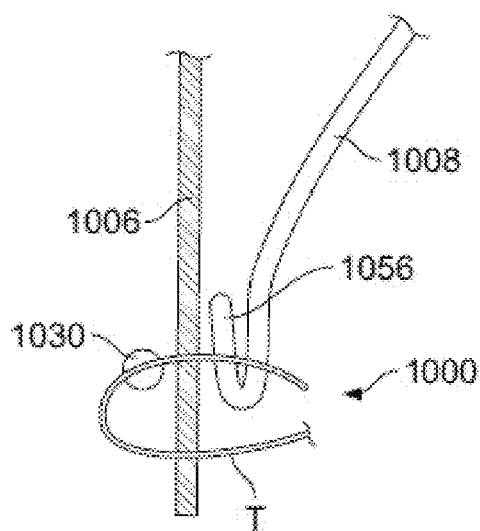
FIG. 10B is a highly schematic cross-sectional view of a portion of another collapsible prosthetic heart valve according to the present invention having a folded leaflet sutured to the underwire and the cuff.
Figure 10C:
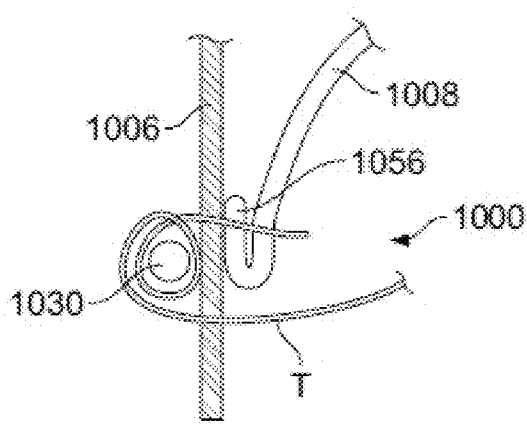
FIG. 10C is a highly schematic cross-sectional view of a portion of a further collapsible prosthetic heart valve according to the present invention having a folded leaflet sutured to the underwire and the cuff.

A second configuration, shown in FIG. 10B, will be referred to as the "pierced" configuration. In the pierced configuration, the suture T begins at the interior of valve 1000 and is passed through the leaflet 1008, the belly flap 1056 and the cuff 1006. Instead of wrapping around underwire 1030, the suture is pierced through underwire 1030 and passed back toward the interior of the valve through the cuff 1006 and under the folded edge of leaflet 1008. Obviously, in this embodiment the underwire 1030 must be formed of a material capable of receiving the suture T therethrough. This stitch pattern may be repeated around the entire circumference of valve 1000 to secure each of leaflets 1008 and underwire 1030 to cuff 1006.

In a third configuration, the underwire 1030 is cinched as shown in FIG. 10C. The "cinched" configuration may begin in a manner similar to the wrapped configuration of FIG. 10A, with suture T passing from the interior of the valve 1000 through leaflet 1008, belly flap 1056 and cuff 1006. Suture T may then be wrapped in a full loop around the underwire 1030 and then passed back to the interior of the valve through cuff 1006 and under the folded edge of leaflet 1008. It will be understood that this cinched configuration is not limited to a single loop around underwire 1030, and that suture T may wrap around the underwire 1030 any number of revolutions as desired before passing back to the interior of the valve.

Figure 11A:
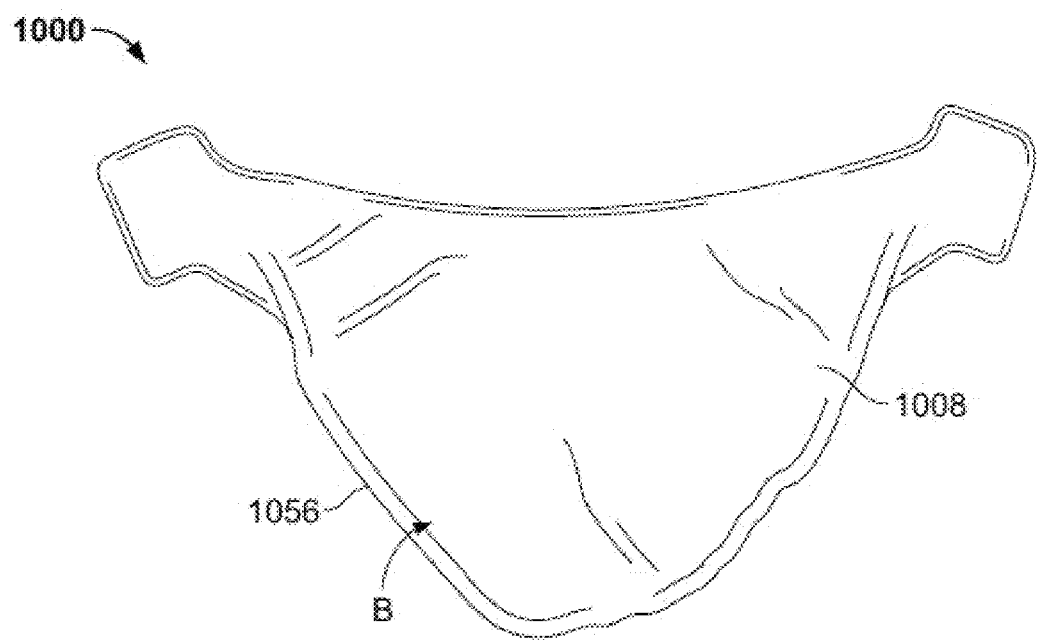
FIG. 11A is a side view of a leaflet folded over itself to produce a belly flap and secured via a reverse-running stitch.
Figure 11B:
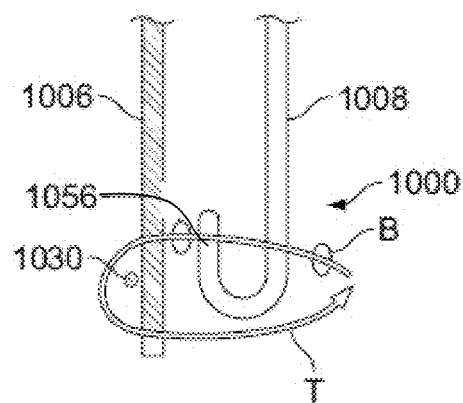
FIG. 11B is a highly schematic cross-sectional view of a portion of a further collapsible prosthetic heart valve according to the present invention having a folded leaflet sutured to the underwire and the cuff through a reverse-running stitch.

In another configuration, shown in FIGS. 11A and 11B, leaflet 1008 is folded over itself to form belly flap 1056 and a reverse-running stitch B holds belly flap 1056 to leaflet 1008 to create a thickened portion, which will then be coupled to cuff 1006. Heart valve 1000 has leaflets 1008 sutured to both an underwire 1030 and a cuff 1006 as shown in FIG. 11B. Specifically, a suture T passes through reverse-running stitch B, leaflet 1008, leaflet belly flap 1056, the other side of revere-running stitch B and cuff 1006. The suture T then wraps around underwire 1030 and is passed back toward the interior of the valve through the cuff 1006 and under the folded edge of leaflet 1008, creating a whip stitch. This stitch pattern may be repeated around the entire circumference of valve 1000 to secure each of leaflets 1008 and underwire 1030 to cuff 1006. Folding leaflet 1008 over itself to create a belly flap and using a reverse-running stitch B to secure the two together produces a thickened portion that provides enhanced structural integrity for attaching the leaflet to cuff 1006 and underwire 1030.

FIGS. 11C-P are highly schematic cross-sectional views of various configurations for attaching underwire 1030 to cuff 1006. As will be appreciated from these figures, suture T may pass through or around any combination of the reverse-running stitch B, leaflet 1008, belly flap 1056, cuff 1006, and underwire 1030. In addition to these configurations, underwire 1030 may be moved to a different location, or multiple underwires may be utilized. For example, a second underwire 1030 may be disposed between leaflet 1008 and belly flap 1056 to form the thickened portion in addition to underwire 1030 disposed outside cuff 1006.

Underwire 1030 could also be disposed inside cuff 1006 (e.g., between cuff 1006 and belly flap 1056) or at any other suitable position so long as it helps redistribute load over the cuff and helps prevent tearing of the cuff.

In other variations, underwire 1030 may be disposed on the outside of the stent struts in certain portions and on the inside of the stent struts in other portions. Underwire 1030 may also be weaved in and out of cuff 1006, and may be attached to the commissure features to provide additional support. Additionally, underwire 1030 need not be continuous and may be formed of discrete portions disposed around the circumference of the heart valve.

Though the previous configurations have shown a leaflet 1008 folded over toward the cuff 1006 to form a belly flap 1056, it will be appreciated that the cuff-leaflet assembly, also referred to as a belly attachment contour, is not limited to this configuration. In other examples, the cuff-leaflet assembly may include a leaflet that is folded away from cuff 1006 to form a belly flap 1056 on the side of the leaflet 1008 opposite the cuff. Additionally, leaflet 1008 of the cuff-leaflet assembly need not form a two-layered belly flap 1056 at all but may lay flat against cuff 1006. It is also contemplated that cuff 1006 itself may be folded over and that multiple reverse-running stitches may be utilized instead of a single stitch as described above.

Figure 12:
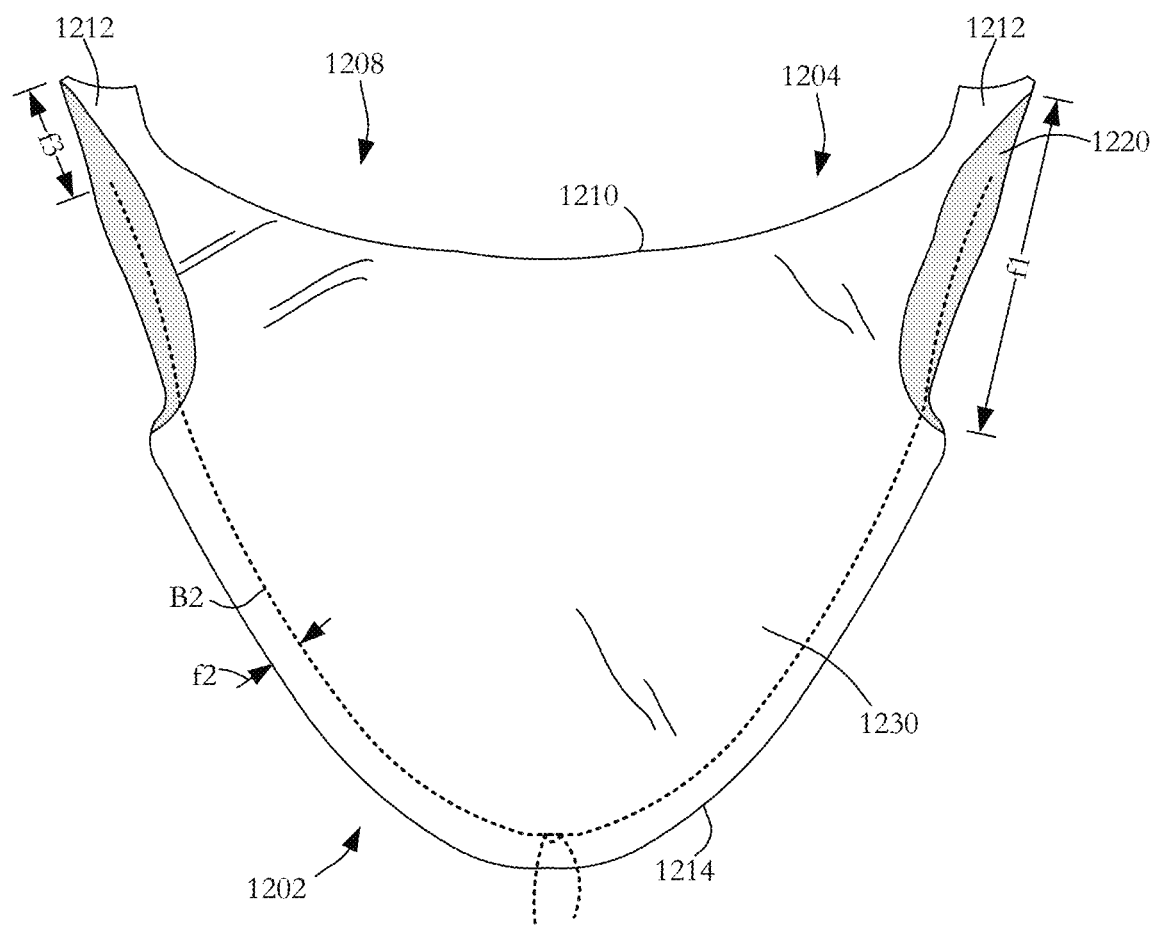
FIG. 12 is a side view of a leaflet having folded portions and an unfolded belly region including a reverse-running stitch.

As shown in FIG. 12, in another embodiment leaflet 1208 is folded along only a part of its belly contour. Leaflet 1208 extends between proximal end 1202 and distal end 1204 and includes a belly 1230 having a free edge 1210 stretching between attachment regions 1212, which couple to the commissure features of a stent. A substantially parabolic belly contour 1214 is formed between attachment regions 1212 on the edge of leaflet 1208 opposite free edge 1210. Portions of belly contour 1214 are folded over to form two-layered folded portions 1220. Folded portions 1220 may be formed with any length f1. In one example, folded portions 1220 each include about ¼ to about ⅓ of the length of belly contour 1214. In some examples, the length t1 of each folded portion 1220 is between about 4 mm and about 8 mm, and may be about 6 mm. Folded portions 1220 may include the end of belly contour 1214 that are closest to attachment regions 1212. Thus, the portion of belly contour 1214 between folded portions 1220 may remain substantially flat. By creating an unfolded region spaced from the end of belly contour 1214, the bulk of the leaflet may be decreased. To reinforce the belly 1230 of leaflet 1208, which will be attached to a cuff, reverse-running stitch B2 may be formed a distance f2 from belly contour 1214 and may follow the curvature of the belly contour. As stitch B2 extends through folded portions 1220 it may secure together the two layers forming folded portions 1220. Reverse-running stitch B2 may terminate prior to reaching free edge 1210 so as not to affect the coaptation of free edge 1210 with the free edges of the other leaflets, which collectively form the valve assembly. Thus, reverse-running stitch B2 may be spaced from free edge 1210 by a distance f3. In at least some embodiments, distance f3 may be between about 0.5 and about 5 mm.

A leaflet having an unfolded belly such as that shown in FIG. 12 may be coupled to a cuff in a variety of configurations. FIGS. 13A-H are highly schematic cross-sectional views of some permutations for attaching an underwire 1330 to a cuff 1306 having an unfolded belly. As will be appreciated from these figures, sutures T2A-H may pass through or around any combination of reverse-running stitches B2, leaflet 1308, underwire 1330, and cuff 1306.

Figure 13A:
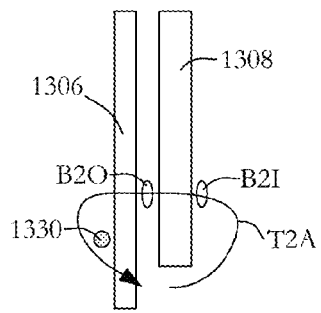
FIGS. 13A-K are highly schematic cross-sectional views of various configurations of attaching an underwire to an unfolded leaflet and a cuff.

In FIG. 13A, suture T2A passes, through inner reverse-running stitch B2I, leaflet 1308, outer reverse-running stitch B2O and cuff 1306, and finally wraps around underwire 1330 before passing through cuff 1306 a second time and under the edge of leaflet 1308. Thus, in this configuration, suture T2A passes through both inner reverse-running stitch B2I and outer reverse-running stitch B2O and wraps around underwire 1330.

Figure 13B:
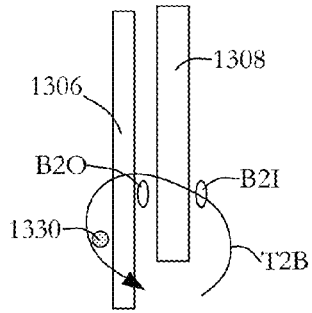

In FIG. 13B, suture T2B passes, through inner reverse-running stitch B2I and leaflet 1308, above outer reverse-running stitch B2O, and through cuff 1306, and finally wraps around underwire 1330 before passing through cuff 1306 a second time and under the edge of leaflet 1308. Thus, in this configuration, suture T2B passes through only inner reverse-running stitch B2I and wraps around both outer reverse-running stitch B2O and underwire 1330.

Figure 13C:
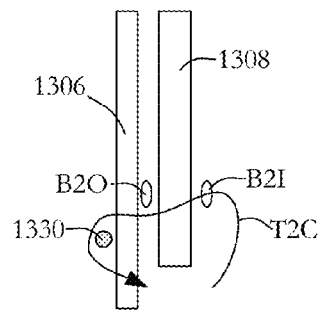

FIG. 13C show a configuration similar to that of FIG. 13B except that suture T2C passes under outer reverse-running stitch B2O instead of above it. Thus, in this configuration, suture T2C passes through only inner reverse-running stitch B2I and wraps around only underwire 1330.

Figure 13D:
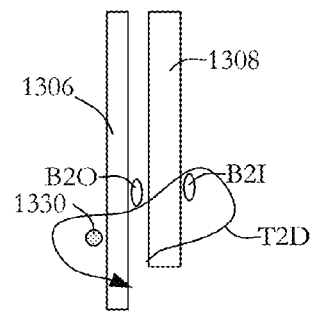

In FIG. 13D, suture T2D first passes inwardly through leaflet 1308, around inner reverse-running stitch B2I and outwardly through leaflet 1308, under outer reverse-running stitch B2O and through cuff 1306, and finally wraps around underwire 1330 before passing through cuff 1306 a second time. Thus, in this configuration, suture T2D does not pass through any reverse-running stitches, wraps around only inner reverse-running stitch B2I and underwire 1330, and passes through leaflet 1308 twice.

Figure 13E:
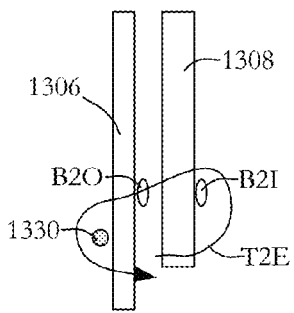

In FIG. 13E, suture T2E passes inwardly through leaflet 1308, around inner reverse-running stitch B2I and outwardly through leaflet 1308, through outer reverse-running stitch B2O and cuff 1306, and finally wraps around underwire 1330 before passing through cuff 1306 a second time. Thus, in this configuration, suture T2E wraps around both inner reverse-running stitch B2I and underwire 1330 and passes through outer reverse-running stitch B2O.

Figure 13F:
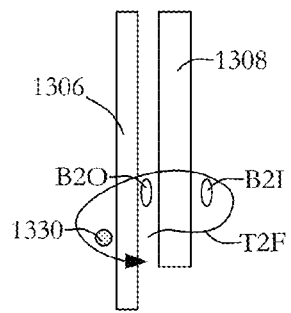

In FIG. 13F, suture T2F passes inwardly through leaflet 1308, above inner reverse-running stitch B2I outwardly through leaflet 1308, above outer reverse-running stitch B2O and through cuff 1306, and finally wraps around underwire 1330 before passing through cuff 1306 a second time. Thus, in this configuration, suture T2F wraps around all of inner reverse-running stitch B2I, outer reverse-running stitch B2O and underwire 1330.

Figure 13G:
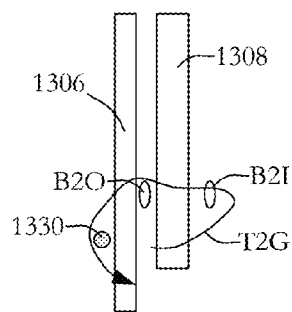

In FIG. 13G, suture T2G passes inwardly through leaflet 1308, through inner reverse-running stitch B2I, outwardly through leaflet 1308, above outer reverse-running stitch B2O and through cuff 1306, and finally wraps around underwire 1330 passing through cuff 1306 a second time. Thus, in this configuration, suture T2G passes through inner reverse-running stitch B2I, and wraps around both outer reverse-running stitch B2O and underwire 1330.

Figure 13H:
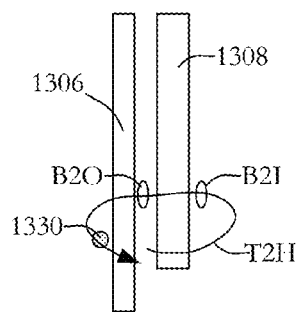

In FIG. 13H, suture T2H passes inwardly through leaflet 1308, through inner reverse-running stitch B2I, outwardly through leaflet 1308, through outer reverse-running stitch B2O, cuff 1306, and underwire 1330, and returns by passing through cuff 1306 a second time. Thus, in this configuration, suture T2H passes through all of inner reverse-running stitch B2I, outer reverse-running stitch B2O and underwire 1330, as well as twice through each of cuff 1306 and leaflet 1308.

Figure 13I:
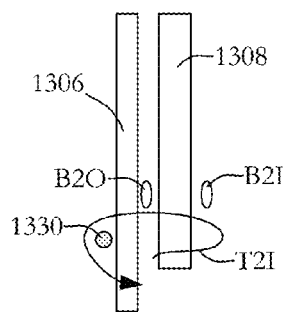

In FIG. 13I, suture T2I passes inwardly through leaflet 1308, under inner reverse-running stitch B2I, outwardly through leaflet 1308, under outer reverse-running stitch B2O and through cuff 1306, and finally wraps around underwire 1330 before passing through cuff 1306 a second time. In this configuration, suture T2I wraps around only underwire 1330.

Figure 13J:
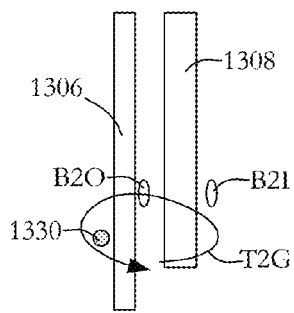

In FIG. 13J, suture T2J passes inwardly through leaflet 1308, under inner reverse-running stitch B2I, outwardly through leaflet 1308, through outer reverse-running stitch B2O and cuff 1306, and finally wraps around underwire 1330 before passing through cuff 1306 a second time. In this configuration, suture T2J wraps around only underwire 1330 and passes through outer reverse-running stitch B2O.

Figure 13K:
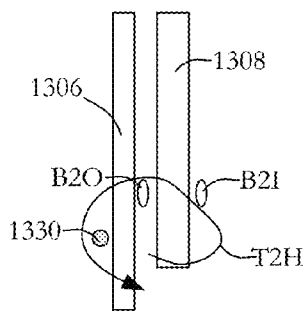

In FIG. 13K, suture T2K passes inwardly through leaflet 1308, under inner reverse-running stitch B2I, outwardly through leaflet 1308, over outer reverse-running stitch B2O and through cuff 1306, and finally wraps around underwire 1330 before passing through cuff 1306 a second time. In this configuration, suture T2K wraps around underwire 1330 and outer reverse-running stitch B2O.

In addition to these configurations, underwire 1330 may be moved to a different location, or multiple underwires may be utilized. Moreover, multiple sutures T2 may be used to couple any combination of cuff 1306, leaflet 1308, reverse-running stitches B2 and underwire 1330 and may be passed through or around any combination of these elements.

Figure 14:
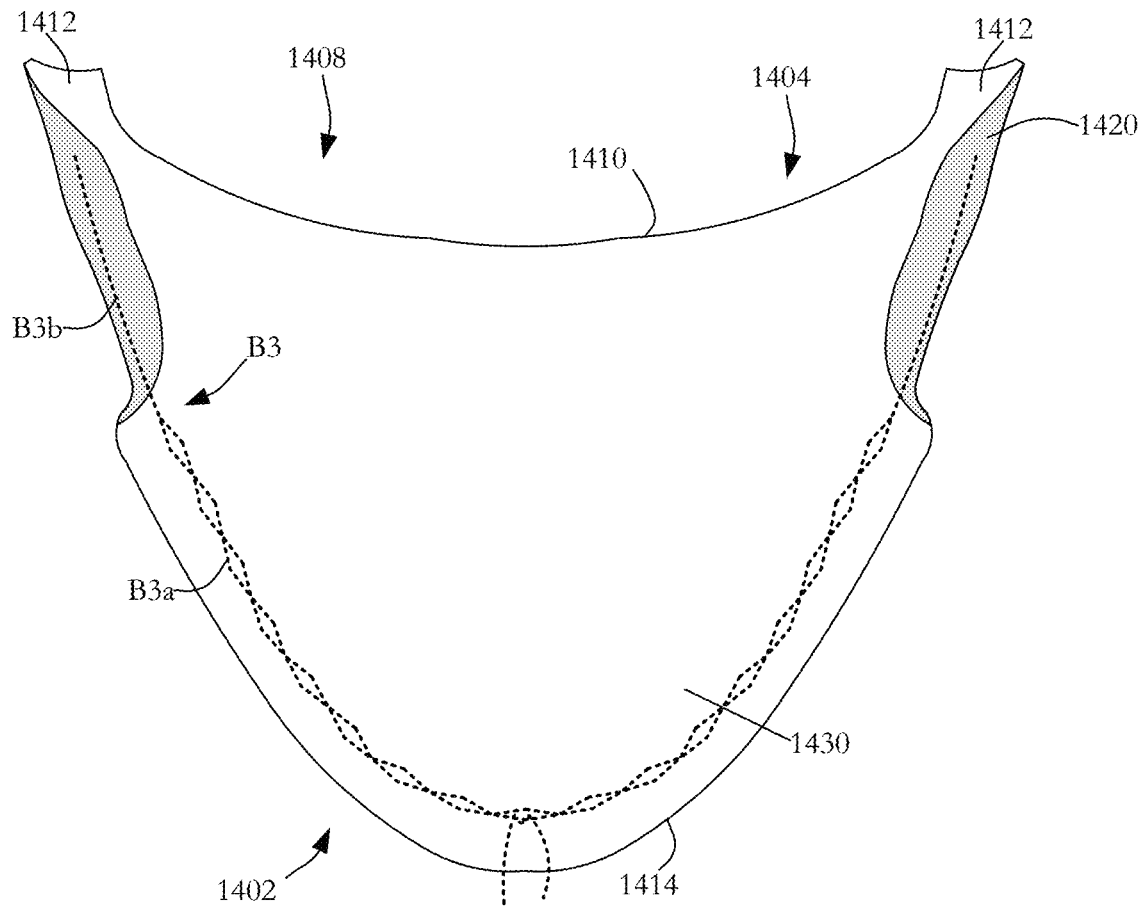
FIG. 14 is a side view of a leaflet having folded portions and an unfolded belly region including a diamond-shaped reverse-running stitch.

FIG. 14 shows another embodiment of a leaflet 1408 that is folded along only a part of its belly contour. Leaflet 1408 extends between proximal end 1402 and distal end 1404 and includes a belly 1430 having a free edge 1410 stretching between attachment regions 1412, which couple to commissure features as described above. A substantially parabolic belly contour 1414 is formed between attachment regions 1412 on the edge of leaflet 1408 opposite free edge 1410. Two portions of belly contour 1414 are folded over to form two-layered folded portions 1420. To reinforce belly 1430, which will be attached to a cuff, a reverse-running stitch B3 may be formed with two segments, B3a and B3b that follows the curvature of belly contour 1414 at a spaced distance therefrom in a manner similar to that described with reference to FIG. 12. Reverse-running stitch B3 is formed with a different pattern than that shown in FIG. 12. Specifically, the first segment B3a of reverse-running stitch B3 has a recurring, substantially diamond-shaped pattern along the belly contour of the leaflet. The selected pattern affects load transfer properties, ease of assembly, and bulkiness. In this case, the pattern of the first segment B3a of reverse-running stitch B3 may provide a larger area to suture into instead of going through/around a single line of reverse-running stitch.

The first segment B3a of reverse-running stitch B3 may terminate prior to reaching folded portions 1420, the layers of which may be secured together by a curved second segment B3b or reverse-running stitch B3. Alternatively, first segment B3a may extend through folded portion 1420. Additionally, reverse-running stitch B3 may terminate prior to reaching free edge 1410 so as not to affect the coaptation of free edge 1410 with the free edges of the other leaflets, which collectively form the valve assembly.

Figure 15:
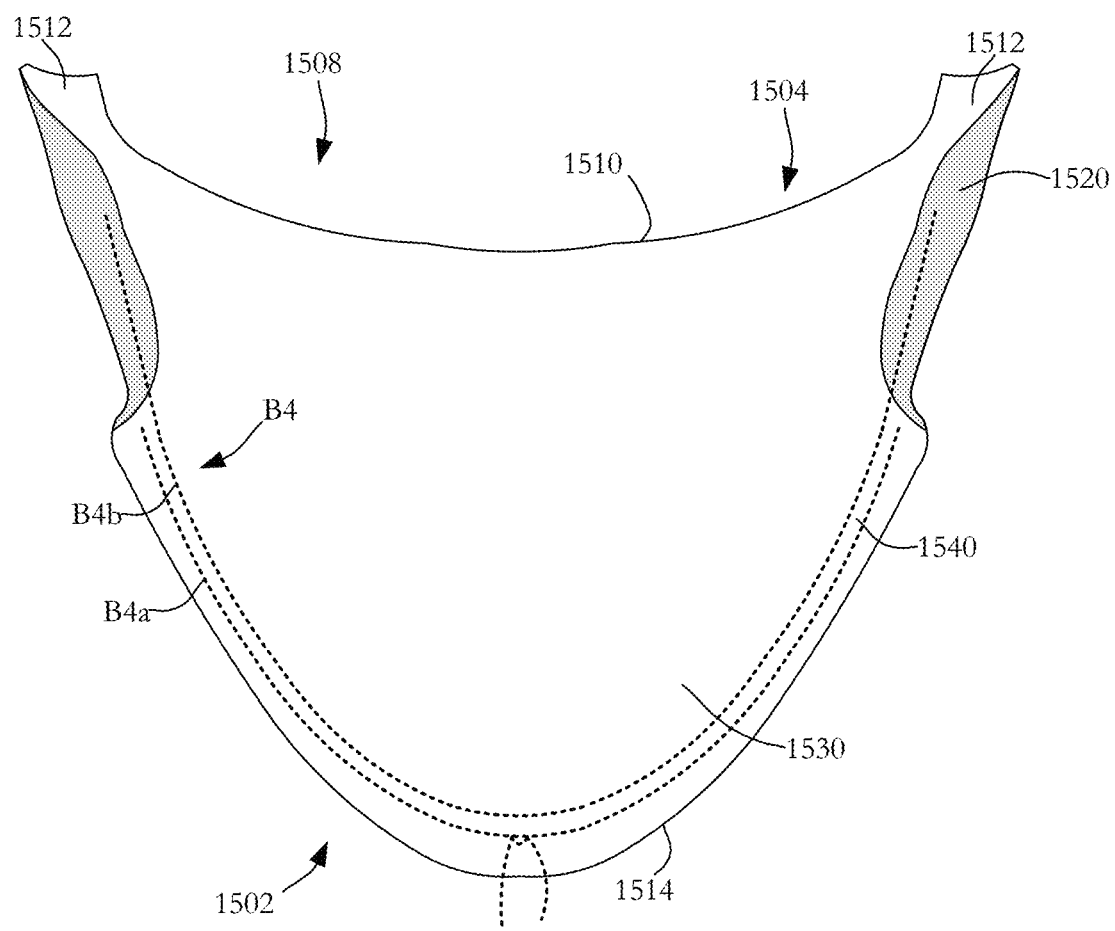
FIG. 15 is a side view of a leaflet having folded portions and an unfolded belly region including a pair of parabolic reverse-running stitches.

FIG. 15 shows another embodiment of a leaflet 1508 that is folded along only part of its belly contour. Leaflet 1508 extends between proximal end 1502 and distal end 1504 and includes a belly 1530 having a free edge 1510 stretching between attachment regions 1512, which couple to commissure features as described above. A substantially parabolic belly contour 1514 is formed between attachment regions 1512 on the edge of leaflet 1508 opposite free edge 1510. Portions of belly contour 1514 are folded over to form two-layered folded portions 1520. To reinforce belly 1530, which will be attached to a cuff, a reverse-running stitch B4 may be formed with two complementary second segments, B4a and B0b that follow the curvature of belly contour 1514 at a spaced distance therefrom. In this embodiment, segments B4a and B0b of reverse-running stitch B4 are not attached to one another.

First segment B4a may be substantially parabolic and may terminate prior to reaching folded portions 1520. Second segment B0b may follow the contour of first segment B0b at a spaced distance therefrom to define a coupling area 1540 therebetween for suturing leaflet 1508 to a cuff. Second segment B0b may extend through folded portions 1520 to secure the two layers of each folded portion together. In either case, reverse-running stitch B4 may terminate prior to reaching free edge 1510 so as not to affect the coaptation of free edge 1510 with the free edges of the other leaflets, which collectively form the valve assembly.

Figure 16:
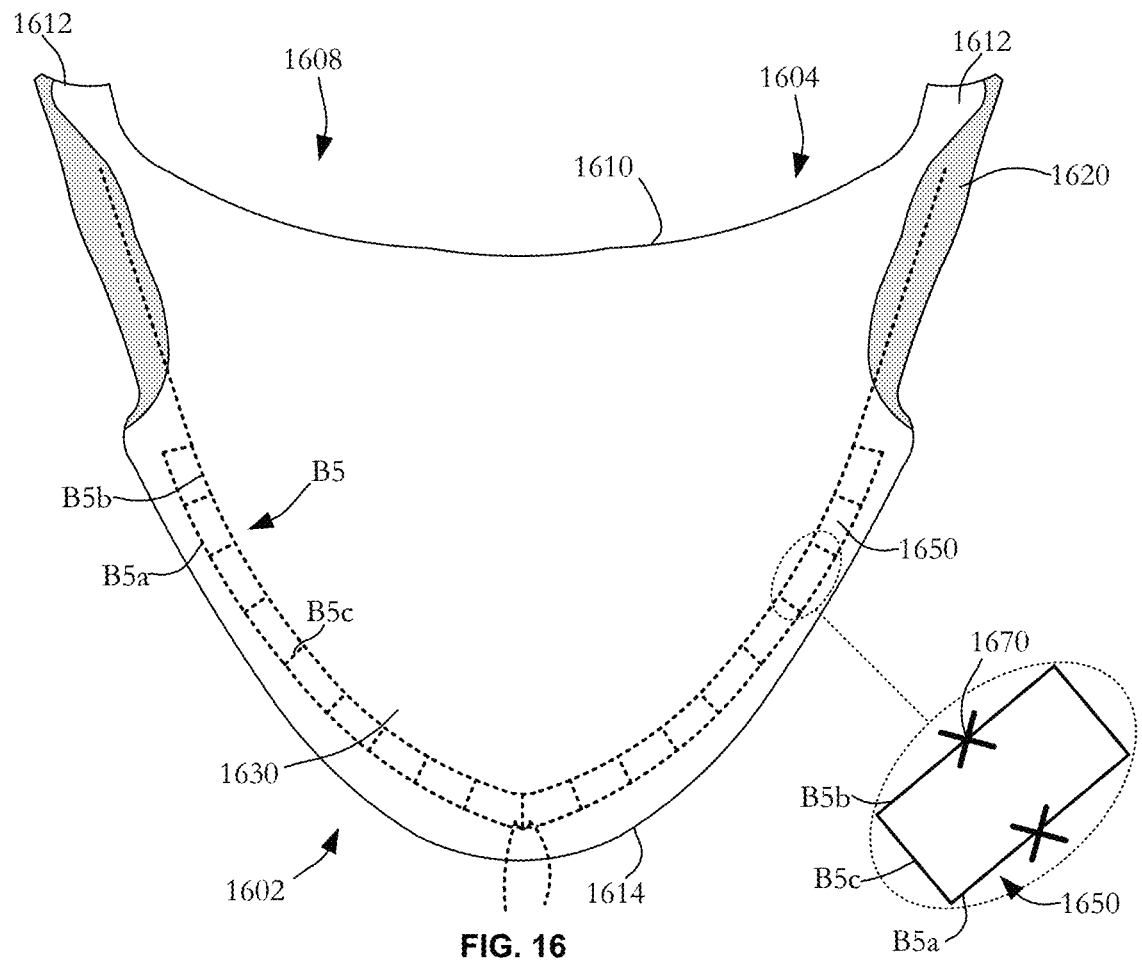
FIG. 16 is a side view of a leaflet having folded portions and an unfolded belly region including a rectangular-shaped reverse-running stitch.

FIG. 16 shows another embodiment that is similar to that of FIG. 15, except for the pattern of reverse-running stitch B5. Leaflet 1608 extends between proximal end 1602 and distal end 1604 and includes a belly 1630 having a free edge 1610 stretching between attachment regions 1612, and a substantially parabolic belly contour 1614 formed between attachment regions 1612 on the edge of leaflet 1608 opposite free edge 1610. Reverse-running stitch B5 may be formed with two complementary segments, B5a and B5b that follow the curvature of belly contour 1614 at a spaced distance therefrom. Segments B5a and B5b of reverse-running stitch B5 are attached to one another by segments B5c, thereby creating a number of coupling rectangles 1650 for receiving sutures to couple leaflet 1608 to a cuff.

First segment B5a may be substantially parabolic and may terminate prior to reaching folded portion 1620. Second segment B5b may follow the contour of first segment B5b at a spaced distance therefrom, and may extend through folded portions 1620 to secure the two layers of each folded portion together. Suture 1670 may couple leaflet 1608 to a cuff through coupling rectangles 1650. Specifically, suture 1670 may be passed through the perimeter of a coupling rectangle 1650. It may be advantageous to pierce the perimeter of coupling rectangle 1650 without piercing through the interior of coupling rectangle 1650 more than once and without piercing the belly 1630 in regions outside of coupling rectangle 1650.

Figure 17:
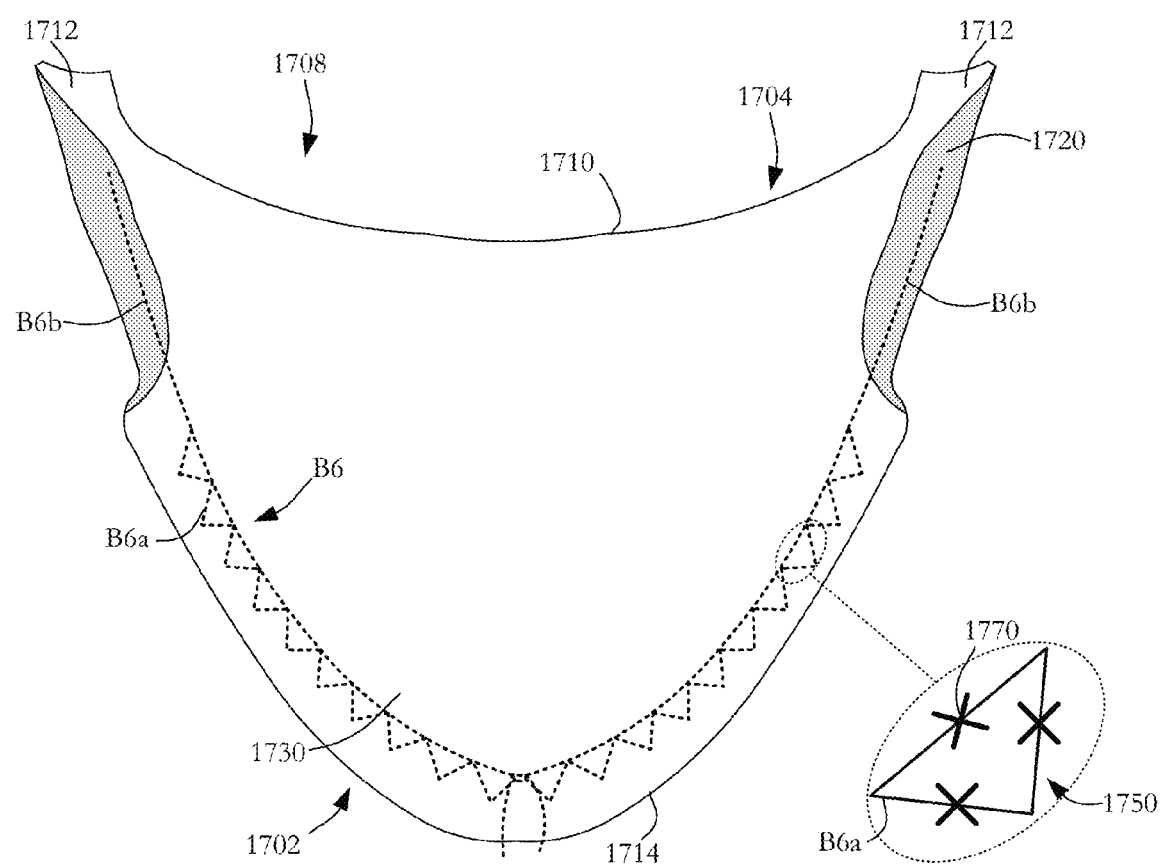
FIG. 17 is a side view of a leaflet having folded portions and an unfolded belly region including a triangle-shaped reverse-running stitch.

FIG. 17 shows another embodiment that is similar to that of FIG. 16, except for the pattern of reverse-running stitch B6. Leaflet 1708 extends between proximal end 1702 and distal end 1704 and includes a belly 1730 having a free edge 1710 stretching between attachment regions 1712, and a substantially parabolic belly contour 1714 formed between attachment regions 1712 on the edge of leaflet 1708 opposite free edge 1710. Reverse-running stitch B6 may be formed with two segments, B6a and B6b that follow the curvature of belly contour 1714 at a spaced distance therefrom.

First segment B6a of reverse-running stitch B6 may include a recurring triangular pattern for accepting a suture therethrough. Suture 1770 may couple leaflet 1708 to a cuff through coupling triangles 1750. Specifically, suture 1770 may be passed through the perimeter of a coupling triangle 1750. It may be advantageous to pierce the perimeter of coupling triangle 1750 without piercing through the interior of coupling triangle 1750 more than once and without piercing the belly 1730 in regions outside of coupling triangle 1750.

In operation, any of the embodiments of the prosthetic heart valve described above may be used to replace a native heart valve, such as the aortic valve. The prosthetic heart valve may be delivered to the desired site (e.g., near a native aortic annulus) using any suitable delivery device. During delivery, the prosthetic heart valve is disposed inside the delivery device in the collapsed condition. The delivery device may be introduced into a patient using a transfemoral, transapical, transseptal, transradial, transaortic, transsubclavian or other percutaneous approach. Once the delivery device has reached the target site, the user may deploy the prosthetic heart valve. Upon deployment, the prosthetic heart valve expands into secure engagement within the native aortic annulus. When the prosthetic heart valve has been properly positioned inside the heart, it works as a one-way valve, allowing blood to flow in one direction and preventing blood from flowing in the opposite direction.

Although the invention herein has been described with reference to particular embodiments, it is to be understood that these embodiments are merely illustrative of the principles and applications of the present invention. For example, in some embodiments, the underwire may include certain anchoring features, such as barbs for anchoring the heart valve or for valve-in-valve implantation. In at least some other embodiments, the underwire may include a surface finish or be doped with drugs or other material to ensure tissue ingrowth and sealing. Moreover, while the preceding discussion has provided examples by way of folded leaflets, it will be understood that the leaflet need not be folded and that the heart valve may instead include a belly attachment contour having an unfolded leaflet instead of a folded leaflet. It is therefore to be understood that numerous modifications may be made to the illustrative embodiments and that other arrangements may be devised without departing from the spirit and scope of the present invention as defined by the appended claims.

In some embodiments, a prosthetic heart valve includes a stent having a collapsed condition and an expanded condition, the stent having a proximal end, a distal end and a plurality of commissure features. The heart valve further includes a valve assembly secured to the stent, the valve assembly including a cuff and a plurality of leaflets, each of the leaflets having a free edge having a first end and a second end, and a second edge secured to the cuff, the second edge having a first end, a second end, a first folded portion adjacent the first end, a second folded portion adjacent the second end, and an unfolded portion between the first and second folded portions. The first and second folded portions couple the leaflet to ones of the commissure features.

In some examples, a reinforcement may be disposed along the unfolded portion of each of the leaflets. The reinforcement may include a reverse-running stitch. The reverse-running stitch may be formed in a substantially parabolic pattern that follows the curvature of the unfolded portion. The reverse-running stitch may include multiple segments and at least one of the segments extends over one of the first folded portion and the second folded portion. The reverse-running stitch may include a recurring diamond-shaped pattern. The reverse-running stitch may include a recurring rectangular pattern. The reverse-running stitch may include a recurring triangular pattern. The reverse-running stitch may be spaced away from the free edge of the leaflet. The reverse-running stitch may be spaced away from the free edge of the leaflet. The reverse-running stitch may include two complementary parabolic curves defining a coupling region therebetween for receiving sutures. A reinforcing underwire may be coupled to the cuff. The underwire may form a repeating parabolic pattern about the circumference of the cuff.

In some embodiments, a prosthetic valve assembly includes a substantially cylindrical cuff, a plurality of leaflets disposed inside the cuff, a reverse-running stitch coupled to unfolded portions of each of the leaflets, the reverse-running stitch having an outer part disposed between the cuff and each of the leaflets and an inner part disposed on an opposite side of each of the leaflets and a suture for coupling the cuff to each of the leaflets.

In some examples, an underwire may be disposed on an abluminal surface of the cuff. The suture may pass through each of the cuff, ones of the leaflets, the inner part of the reverse-running stitch, the outer part of the reverse-running stitch and the underwire. The suture may pass over the inner part of the reverse-running stitch, the outer part of the reverse-running stitch and the underwire, and passes through each of the cuff and ones of the leaflets. The suture may wrap around the underwire. The suture may pass through one of the inner part and the outer part of the reverse-running stitch. The suture may pass over one of the inner part and the outer part of the reverse-running stitch.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve, comprising:
   a stent having a collapsed condition and an expanded condition, the stent having a proximal end, a distal end and a plurality of commissure features;
   a valve assembly secured to the stent, the valve assembly including a cuff and a plurality of leaflets, each of the leaflets having a free edge, and a second edge opposite the free edge and being secured to the cuff, the second edge having a first end, a second end, a first folded portion adjacent the first end, a second folded portion adjacent the second end, and an unfolded portion between the first and second folded portions, the first and second folded portions coupling the leaflet to at least one of the commissure features; and
   wherein each leaflet comprises a continuous reinforcement spaced away from the second edge and following the curvature of the second edge, each continuous reinforcement being disposed along the unfolded portion of the leaflet and extending over the first and second folded portions to secure the first and second folded portions to other portions of the leaflet.

2. The prosthetic heart valve according to claim 1, wherein each continuous reinforcement comprises a reverse-running stitch.

3. The prosthetic heart valve according to claim 2, wherein the reverse-running stitch is formed in a substantially parabolic pattern that follows the curvature of the unfolded portion.

4. The prosthetic heart valve according to claim 2, wherein the reverse-running stitch comprises multiple segments.

5. The prosthetic heart valve according to claim 2, wherein the reverse-running stitch comprises a recurring diamond-shaped pattern.

6. The prosthetic heart valve according to claim 2, wherein the reverse-running stitch comprises a recurring rectangular pattern.

7. The prosthetic heart valve according to claim 2, wherein the reverse-running stitch comprises a recurring triangular pattern.

8. The prosthetic heart valve according to claim 2, wherein the reverse-running stitch is spaced away from the free edge of the leaflet.

9. The prosthetic heart valve according to claim 1, further comprising a reinforcing underwire coupled to the cuff.

10. The prosthetic heart valve according to claim 9, wherein the underwire forms a repeating parabolic pattern about the circumference of the cuff.

11. A prosthetic valve assembly, comprising:
a substantially cylindrical cuff;
a plurality of leaflets disposed inside the cuff, each of the plurality of leaflets having a free edge, and a second edge opposite the free edge, the second edge having an unfolded portion extending between two folded portions;
a reverse-running stitch coupled to unfolded and folded portions of each of the leaflets, the reverse-running stitch having an outer part disposed between the cuff and each of the leaflets and an inner part disposed on an opposite side of each of the leaflets; and
a suture for coupling the cuff to each of the leaflets.

12. The valve assembly according to claim 11, further comprising an underwire disposed on an abluminal surface of the cuff.

13. The valve assembly according to claim 12, wherein the suture passes through each of the cuff, at least one of the leaflets, the inner part of the reverse-running stitch, the outer part of the reverse-running stitch and the underwire.

14. The valve assembly according to claim 12, wherein the suture passes over the inner part of the reverse-running stitch, the outer part of the reverse-running stitch and the underwire, and passes through each of the cuff and at least one of the leaflets.

15. The valve assembly according to claim 12, wherein the suture wraps around the underwire.

16. The valve assembly according to claim 12, wherein the suture passes through one of the inner part and the outer part of the reverse-running stitch.

17. The valve assembly according to claim 12, wherein the suture passes over one of the inner part and the outer part of the reverse-running stitch.

* * * * *